(12) United States Patent
Kleinfeld et al.

(10) Patent No.: US 9,529,003 B2
(45) Date of Patent: Dec. 27, 2016

(54) DEVELOPMENT AND USE OF FLUORESCENT PROBES OF UNBOUND BILIRUBIN

(75) Inventors: Alan Marc Kleinfeld, La Jolla, CA (US); Andrew Henry Huber, Encinitas, CA (US); James Patrick Kampf, San Diego, CA (US); Thomas Kwan, San Diego, CA (US); Baolong Zhu, San Diego, CA (US)

(73) Assignee: Alan Marc Kleinfeld, La Jolla, CA (US)

( * ) Notice: Subject to any disclaimer, the term of this patent is extended or adjusted under 35 U.S.C. 154(b) by 70 days.

(21) Appl. No.: 14/238,144

(22) PCT Filed: Aug. 24, 2012

(86) PCT No.: PCT/US2012/052395
§ 371 (c)(1),
(2), (4) Date: Feb. 10, 2014

(87) PCT Pub. No.: WO2013/032953
PCT Pub. Date: Mar. 7, 2013

(65) Prior Publication Data
US 2015/0044692 A1    Feb. 12, 2015

Related U.S. Application Data

(60) Provisional application No. 61/527,849, filed on Aug. 26, 2011.

(51) Int. Cl.
| | | |
|---|---|---|
| *A61K 38/00* | (2006.01) |
| *G01N 33/72* | (2006.01) |
| *G01N 33/533* | (2006.01) |
| *G01N 33/92* | (2006.01) |
| *G01N 21/64* | (2006.01) |
| *G01N 33/58* | (2006.01) |
| *C07K 14/47* | (2006.01) |

(52) U.S. Cl.
CPC ............ *G01N 33/728* (2013.01); *C07K 14/47* (2013.01); *G01N 21/6428* (2013.01); *G01N 33/533* (2013.01); *G01N 33/582* (2013.01); *G01N 33/92* (2013.01); *G01N 2800/52* (2013.01); *Y10T 436/146666* (2015.01)

(58) Field of Classification Search
None
See application file for complete search history.

(56) References Cited

U.S. PATENT DOCUMENTS

| 7,674,752 B2 | 3/2010 | He et al. |
| 9,164,109 B2 | 10/2015 | Kleinfeld et al. |
| 2005/0244864 A1 | 11/2005 | Kleinfeld et al. |
| 2006/0257938 A1 | 11/2006 | Kleinfeld et al. |
| 2009/0318299 A1 | 12/2009 | Kleinfeld et al. |
| 2010/0062948 A1 | 3/2010 | Kleinfeld et al. |
| 2010/0298162 A1 | 11/2010 | Kleinfeld et al. |
| 2011/0245093 A1 | 10/2011 | He et al. |

FOREIGN PATENT DOCUMENTS

| CN | 101971009 A | 2/2011 |
| JP | 2004-506898 A | 3/2004 |
| WO | WO 2005/093103 A | 10/2005 |
| WO | WO 2008/060841 A2 | 5/2008 |
| WO | WO 2009/092047 | * 7/2009 |
| WO | WO 2009/092047 A1 | 7/2009 |

OTHER PUBLICATIONS

Partial Supplementary European Search Report for European Patent Application No. 12827317.4, issued on Mar. 11, 2015.
International Search Report for International Application No. PCT/US2012/052395, mailed on Jun. 1, 2013.
Huber et al., "Fatty acid-specific fluorescent probes and their use in resolving mixtures of unbound free fatty acids in equilibrium with albumin," Biochemistry, vol. 45(48), pp. 14263-14274 (Dec. 5, 2006).
Office Action issued in Chinese Patent Application No. 201280041789.4, issued on Jun. 5, 2015.

\* cited by examiner

*Primary Examiner* — Karlheinz R Skowronek
*Assistant Examiner* — Sergio Coffa
(74) *Attorney, Agent, or Firm* — Knobbe, Martens, Olson & Bear, LLP

(57) ABSTRACT

Identification and use of proteins fluorescently labeled and that undergo a change in fluorescence index upon binding bilirubin are described. Probes are disclosed which are labeled at a cysteine or lysine residue and also probes labeled at both cysteine and lysine with two different fluorophores. These probes are useful for determination of unbound bilirubin levels in a fluid sample.

45 Claims, 9 Drawing Sheets

SEQUENCE LISTING

```
<160> NUMBER OF SEQ ID NOS: 76

<210> SEQ ID NO 1
<211> LENGTH: 399
<212> TYPE: DNA
<213> ORGANISM: Rattus norvegicus
<220> FEATURE:
<221> NAME/KEY: CDS
<222> LOCATION: (1)...(399)
<223> OTHER INFORMATION: wild-type rat intestinal fatty acid binding
      protein cDNA sequence

<400> SEQUENCE: 1 atg gca ttt gat ggc act tgg aaa gta tac cgg aat gag aac tat gaa      48
Met Ala Phe Asp Gly Thr Trp Lys Val Tyr Arg Asn Glu Asn Tyr Glu
1               5                   10                  15 aag ttc atg gag aaa atg ggc att aac gtg gtg aag agg aag ctt gga      96
Lys Phe Met Glu Lys Met Gly Ile Asn Val Val Lys Arg Lys Leu Gly
            20                  25                  30
```

```
gct cat gac aac ttg aaa ctg acg atc aca cag gaa gga aat aaa ttc      144
Ala His Asp Asn Leu Lys Leu Thr Ile Thr Gln Glu Gly Asn Lys Phe
        35                  40                  45 aca gtc aaa gaa tca agc aac ttc cga aac att gat gtt gtg ttt gaa      192
Thr Val Lys Glu Ser Ser Asn Phe Arg Asn Ile Asp Val Val Phe Glu
 50                  55                  60 ctc ggc gtc gac ttt gcc tat agt cta gca gat gga aca gaa ctc act      240
Leu Gly Val Asp Phe Ala Tyr Ser Leu Ala Asp Gly Thr Glu Leu Thr
 65                  70                  75                  80 ggg acc ttg acc atg gag gga aat aaa ctt gtt gga aaa ttc aaa cgt      288
Gly Thr Leu Thr Met Glu Gly Asn Lys Leu Val Gly Lys Phe Lys Arg
                 85                  90                  95 gta gac aat gga aag gag ctg att gct gtc cga gag att tct ggt aac      336
Val Asp Asn Gly Lys Glu Leu Ile Ala Val Arg Glu Ile Ser Gly Asn
            100                 105                 110 gaa cta atc caa acc tac aca tat gaa gga gtg gag gcc aag cgc atc      384
Glu Leu Ile Gln Thr Tyr Thr Tyr Glu Gly Val Glu Ala Lys Arg Ile
        115                 120                 125 ttt aag aag gaa tag                                                  399
Phe Lys Lys Glu
    130

<210> SEQ ID NO 2
<211> LENGTH: 131
<212> TYPE: PRT
<213> ORGANISM: Rattus norvegicus
<220> FEATURE:
<221> NAME/KEY: PEPTIDE
<222> LOCATION: (1)...(131)
<223> OTHER INFORMATION: wild-type rat intestinal fatty acid binding
      protein
<220> FEATURE:
<221> NAME/KEY: ACETYLATION
<222> LOCATION: (1)...(1)

<400> SEQUENCE: 2

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
             20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
 50                  55                  60

Gly Val Asp Phe Ala Tyr Ser Leu Ala Asp Gly Thr Glu Leu Thr Gly
 65                  70                  75                  80

Thr Trp Thr Met Glu Gly Asn Lys Leu Val Gly Lys Phe Lys Arg Val
                 85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Glu
    130

<210> SEQ ID NO 3
<211> LENGTH: 139
<212> TYPE: PRT
<213> ORGANISM: Rattus norvegicus
<220> FEATURE:
<221> NAME/KEY: VARIANT
<222> LOCATION: (1)...(139)
```

```
<223> OTHER INFORMATION: rat intestinal fatty acid binding protein with
      substitution of Xaa at one or more of 14, 18, 23,
      25, 27, 31, 36, 38, 55, 60, 72, 73, 74, 78, 102,
      104, 106, 115 and 117
<220> FEATURE:
<221> NAME/KEY: VARIANT
<222> LOCATION: (1)...(139)
<223> OTHER INFORMATION: rat intestinal fatty acid binding protein in
      which one amino acid residue may be substituted with
      cysteine or lysine
<220> FEATURE:
<221> NAME/KEY: VARIANT
<222> LOCATION: (134)...(139)
<223> OTHER INFORMATION: optional 6His tag at N terminus
<220> FEATURE:
<221> NAME/KEY: VARIANT
<222> LOCATION: 14,18,23,25,27,31,36,38,55,60,72-74,78,102,104,106,115,
      117
<223> OTHER INFORMATION: Xaa=any amino acid

<400> SEQUENCE: 3

Ala Phe Asp Gly Thr Trp Lys Val Asp Arg Asn Glu Asn Tyr Glu Lys
 1               5                  10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Ala Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Asp Arg Gly His His His His His
    130                 135

<210> SEQ ID NO 4
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 4

Met Gly Ala Cys Ser Gly Gly
 1               5

<210> SEQ ID NO 5
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 5

Met Gly Ser Ala Gly Cys Gly
 1               5

<210> SEQ ID NO 6
<211> LENGTH: 7
<212> TYPE: PRT
```

```
<213> ORGANISM: Artificial Sequence
<220> FEATURE:
<223> OTHER INFORMATION: chemically synthesized linker

<400> SEQUENCE: 6

Met Gly Gly Gly Gly Cys Cys
 1               5

<210> SEQ ID NO 7
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 7

Met Gly Gly Ser Gly Gly Cys
 1               5

<210> SEQ ID NO 8
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 8

Met Gly Asp Thr Ala Gly Cys
 1               5

<210> SEQ ID NO 9
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 9

Met Gly Gly Asp Cys Gly Gly
 1               5

<210> SEQ ID NO 10
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 10

Met Gly Gly Cys Ser Gly Ala
 1               5

<210> SEQ ID NO 11
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 11

Met Gly Gly Gly Asp Gly Cys
 1               5

<210> SEQ ID NO 12
<211> LENGTH: 7
<212> TYPE: PRT
<213> ORGANISM: Artificial Sequence
```

```
<220> FEATURE:
<223> OTHER INFORMATION: chemically synthesized linker

<400> SEQUENCE: 12

Met Gly Ser Ser Asn Ser Cys
1               5

<210> SEQ ID NO 13
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 13

Met Gly Ser Asp Cys Ala Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 14

Met Gly Asp Thr Asn Cys Gly
1               5

<210> SEQ ID NO 15
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 15

Met Gly Gly Ser Gly Cys Ser
1               5

<210> SEQ ID NO 16
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 16

Met Gly Gly Cys Gly Cys Gly
1               5

<210> SEQ ID NO 17
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 17

Met Gly Ala Asn Ala Cys Gly
1               5

<210> SEQ ID NO 18
<211> LENGTH: 7
<212> TYPE: PRT
<213> ORGANISM: Artificial Sequence
<220> FEATURE:
```

<223> OTHER INFORMATION: chemically synthesized linker

<400> SEQUENCE: 18

Met Gly Gly Gly Ala Cys Gly
1               5

<210> SEQ ID NO 19
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 19

Met Gly Gly Asn Cys Gly Gly
1               5

<210> SEQ ID NO 20
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 20

Met Gly Cys Gly Gly Ser Cys
1               5

<210> SEQ ID NO 21
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 21

Met Gly Gly Ser Thr Ser Cys
1               5

<210> SEQ ID NO 22
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 22

Met Gly Asp Gly Gly Cys Ser
1               5

<210> SEQ ID NO 23
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 23

Met Gly Ala Thr Ser Cys Gly
1               5

<210> SEQ ID NO 24
<211> LENGTH: 7
<212> TYPE: PRT
<213> ORGANISM: Artificial Sequence
<220> FEATURE:
<223> OTHER INFORMATION: chemically synthesized linker

```
<400> SEQUENCE: 24

Met Gly Ala Ser Cys Gly Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: chemically synthesized linker

<400> SEQUENCE: 25

Met Gly Asp Gly Ala Cys Gly
1               5

<210> SEQ ID NO 26
<211> LENGTH: 9
<212> TYPE: PRT
<213> ORGANISM: Artificial Sequence
<220> FEATURE:
<223> OTHER INFORMATION: chemically synthesized linker

<400> SEQUENCE: 26

Gly Gly Ser Gly Ser Gly Ser Gly Gly
1               5

<210> SEQ ID NO 27
<211> LENGTH: 25
<212> TYPE: PRT
<213> ORGANISM: Artificial Sequence
<220> FEATURE:
<223> OTHER INFORMATION: chemically synthesized linker

<400> SEQUENCE: 27

Gly Gly Gly Ser Gly Gly Gly Ser Gly Gly Thr Gly Gly Gly Ser
1               5                   10                  15

Gly Gly Gly Arg Arg Ala Asp Ala Ala
            20                  25

<210> SEQ ID NO 28
<211> LENGTH: 11
<212> TYPE: PRT
<213> ORGANISM: Artificial Sequence
<220> FEATURE:
<223> OTHER INFORMATION: chemically synthesized linker

<400> SEQUENCE: 28

Ser Arg Ala Trp Arg His Pro Gln Phe Gly Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: chemically synthesized linker

<400> SEQUENCE: 29

Arg Ala Phe Ile Ala Ser Arg Arg Ile Arg Arg Pro
1               5                   10

<210> SEQ ID NO 30
<211> LENGTH: 9
<212> TYPE: PRT
<213> ORGANISM: Artificial Sequence
```

```
<220> FEATURE:
<223> OTHER INFORMATION: chemically synthesized linker

<400> SEQUENCE: 30

Arg Leu Leu Leu Arg Arg Leu Arg Arg
 1               5

<210> SEQ ID NO 31
<211> LENGTH: 11
<212> TYPE: PRT
<213> ORGANISM: Artificial Sequence
<220> FEATURE:
<223> OTHER INFORMATION: chemically synthesized linker

<400> SEQUENCE: 31

Pro Ser Asn Thr Asn His Asn Ser Asn Ser Asn
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: chemically synthesized linker

<400> SEQUENCE: 32

Ser His Arg Ala Thr Pro Asn Thr Ser Pro His
 1               5                  10

<210> SEQ ID NO 33
<211> LENGTH: 132
<212> TYPE: PRT
<213> ORGANISM: Rattus norvegicus

<400> SEQUENCE: 33

Met Ala Phe Asp Gly Thr Trp Lys Val Tyr Arg Asn Glu Asn Tyr Glu
 1               5                  10                  15

Lys Phe Met Glu Lys Met Gly Ile Asn Val Val Lys Arg Lys Leu Gly
                20                  25                  30

Ala His Asp Asn Leu Lys Leu Thr Ile Thr Gln Glu Gly Asn Lys Phe
            35                  40                  45

Thr Val Lys Glu Ser Ser Asn Phe Arg Asn Ile Asp Val Val Phe Glu
        50                  55                  60

Leu Gly Val Asp Phe Ala Tyr Ser Leu Ala Asp Gly Thr Glu Leu Thr
 65                  70                  75                  80

Gly Thr Leu Thr Met Glu Gly Asn Lys Leu Val Gly Lys Phe Lys Arg
                85                  90                  95

Val Asp Asn Gly Lys Glu Leu Ile Ala Val Arg Glu Ile Ser Gly Asn
            100                 105                 110

Glu Leu Ile Gln Thr Tyr Thr Tyr Glu Gly Val Glu Ala Lys Arg Ile
        115                 120                 125

Phe Lys Lys Glu
    130

<210> SEQ ID NO 34
<211> LENGTH: 26
<212> TYPE: PRT
<213> ORGANISM: Artificial Sequence
<220> FEATURE:
<223> OTHER INFORMATION: chemically synthesized linker

<400> SEQUENCE: 34
```

Ala Ala Ser His His His His His Ser His Arg Ala Thr Pro Asn
1               5                   10                  15

Thr Ser Pro His His His His His His
            20              25

<210> SEQ ID NO 35
<211> LENGTH: 139
<212> TYPE: PRT
<213> ORGANISM: Rattus norvegicus
<220> FEATURE:
<221> NAME/KEY: VARIANT
<222> LOCATION: (1)...(139)
<223> OTHER INFORMATION: BL22P1B11
<220> FEATURE:
<221> NAME/KEY: VARIANT
<222> LOCATION: (14)...(14)
<223> OTHER INFORMATION: Tyr->Arg
<220> FEATURE:
<221> NAME/KEY: VARIANT
<222> LOCATION: (18)...(18)
<223> OTHER INFORMATION: Met-> Leu
<220> FEATURE:
<221> NAME/KEY: VARIANT
<222> LOCATION: (25)...(25)
<223> OTHER INFORMATION: Val-> Cys
<220> FEATURE:
<221> NAME/KEY: VARIANT
<222> LOCATION: (27)...(27)
<223> OTHER INFORMATION: Lys-> Ala
<220> FEATURE:
<221> NAME/KEY: VARIANT
<222> LOCATION: (38)...(38)
<223> OTHER INFORMATION: Leu-> Val
<220> FEATURE:
<221> NAME/KEY: VARIANT
<222> LOCATION: (60)...(60)
<223> OTHER INFORMATION: Val-> Arg
<220> FEATURE:
<221> NAME/KEY: VARIANT
<222> LOCATION: (72)...(72)
<223> OTHER INFORMATION: Leu-> Ala
<220> FEATURE:
<221> NAME/KEY: VARIANT
<222> LOCATION: (73)...(73)
<223> OTHER INFORMATION: Ala-> Phe
<220> FEATURE:
<221> NAME/KEY: VARIANT
<222> LOCATION: (106)...(106)
<223> OTHER INFORMATION: Arg-> Leu
<220> FEATURE:
<221> NAME/KEY: VARIANT
<222> LOCATION: (115)...(115)
<223> OTHER INFORMATION: Gln-> Arg
<220> FEATURE:
<221> NAME/KEY: VARIANT
<222> LOCATION: (117)...(117)
<223> OTHER INFORMATION: Tyr -> Asp
<220> FEATURE:
<221> NAME/KEY: UNSURE
<222> LOCATION: (0)...(0)
<223> OTHER INFORMATION: 6His tag at N terminus

<400> SEQUENCE: 35

Ala Phe Asp Gly Thr Trp Lys Val Asp Arg Asn Glu Asn Arg Glu Lys
1               5                   10                  15

Phe Leu Glu Lys Met Gly Ile Asn Cys Val Ala Arg Lys Leu Gly Ala
            20                  25                  30

His Asp Asn Leu Lys Val Thr Ile Thr Gln Glu Gly Asn Lys Phe Thr
        35                  40                  45

Val Lys Glu Ser Ser Asn Phe Arg Asn Ile Asp Arg Val Phe Glu Leu
    50                  55                  60

Gly Val Asp Phe Ala Tyr Ser Ala Phe Asp Gly Thr Glu Leu Thr Gly

```
         65                  70                  75                  80
Thr Trp Thr Met Glu Gly Asn Lys Leu Val Gly Lys Phe Lys Arg Val
                    85                  90                  95

Asp Asn Gly Lys Glu Leu Ile Ala Val Leu Glu Ile Ser Gly Asn Glu
                100                 105                 110

Leu Ile Arg Thr Asp Thr Tyr Glu Gly Val Glu Ala Lys Arg Ile Phe
                115                 120                 125

Lys Lys Asp Arg Gly His His His His His His
        130                 135

<210> SEQ ID NO 36
<211> LENGTH: 139
<212> TYPE: PRT
<213> ORGANISM: Rattus norvegicus
<220> FEATURE:
<221> NAME/KEY: VARIANT
<222> LOCATION: (1)...(139)
<223> OTHER INFORMATION: L24P19C7
<220> FEATURE:
<221> NAME/KEY: VARIANT
<222> LOCATION: (14)...(14)
<223> OTHER INFORMATION: Tyr->Arg
<220> FEATURE:
<221> NAME/KEY: VARIANT
<222> LOCATION: (18)...(18)
<223> OTHER INFORMATION: Met-> Leu
<220> FEATURE:
<221> NAME/KEY: VARIANT
<222> LOCATION: (38)...(38)
<223> OTHER INFORMATION: Leu-> Val
<220> FEATURE:
<221> NAME/KEY: VARIANT
<222> LOCATION: (60)...(60)
<223> OTHER INFORMATION: Val-> Arg
<220> FEATURE:
<221> NAME/KEY: VARIANT
<222> LOCATION: (72)...(72)
<223> OTHER INFORMATION: Leu->Ala
<220> FEATURE:
<221> NAME/KEY: VARIANT
<222> LOCATION: (73)...(73)
<223> OTHER INFORMATION: Ala-> Phe
<220> FEATURE:
<221> NAME/KEY: VARIANT
<222> LOCATION: (106)...(106)
<223> OTHER INFORMATION: Arg-> Cys
<220> FEATURE:
<221> NAME/KEY: VARIANT
<222> LOCATION: (115)...(115)
<223> OTHER INFORMATION: Gln->Arg
<220> FEATURE:
<221> NAME/KEY: VARIANT
<222> LOCATION: (117)...(117)
<223> OTHER INFORMATION: Tyr-> Asp
<220> FEATURE:
<221> NAME/KEY: UNSURE
<222> LOCATION: (0)...(0)
<223> OTHER INFORMATION: 6His tag at N terminus

<400> SEQUENCE: 36

Ala Phe Asp Gly Thr Trp Lys Val Asp Arg Asn Glu Asn Arg Glu Lys
 1               5                  10                  15

Phe Leu Glu Lys Met Gly Ile Asn Val Val Lys Arg Lys Leu Gly Ala
                20                  25                  30

His Asp Asn Leu Lys Val Thr Ile Thr Gln Glu Gly Asn Lys Phe Thr
                35                  40                  45

Val Lys Glu Ser Ser Asn Phe Arg Asn Ile Asp Arg Val Phe Glu Leu
        50                  55                  60

Gly Val Asp Phe Ala Tyr Ser Ala Phe Asp Gly Thr Glu Leu Thr Gly
```

```
                65                  70                  75                  80
Thr Trp Thr Met Glu Gly Asn Lys Leu Val Gly Lys Phe Lys Arg Val
                        85                  90                  95

Asp Asn Gly Lys Glu Leu Ile Ala Val Cys Glu Ile Ser Gly Asn Glu
                100                 105                 110

Leu Ile Arg Thr Asp Thr Tyr Glu Gly Val Glu Ala Lys Arg Ile Phe
                115                 120                 125

Lys Lys Asp Arg Gly His His His His His His
    130                 135
```

<210> SEQ ID NO 37
<211> LENGTH: 4
<212> TYPE: PRT
<213> ORGANISM: Artificial Sequence
<220> FEATURE:
<223> OTHER INFORMATION: N-terminus of SEQ ID NO: 3 (4 amino acids)

<400> SEQUENCE: 37

```
Met Ala Phe Asp
 1
```

<210> SEQ ID NO 38
<211> LENGTH: 5
<212> TYPE: PRT
<213> ORGANISM: Artificial Sequence
<220> FEATURE:
<223> OTHER INFORMATION: chemically synthesized linker

<400> SEQUENCE: 38

```
Met Gly Ile Phe Asp
 1               5
```

<210> SEQ ID NO 39
<211> LENGTH: 5
<212> TYPE: PRT
<213> ORGANISM: Artificial Sequence
<220> FEATURE:
<223> OTHER INFORMATION: chemically synthesized linker

<400> SEQUENCE: 39

```
Met Gly Cys Phe Asp
 1               5
```

<210> SEQ ID NO 40
<211> LENGTH: 10
<212> TYPE: PRT
<213> ORGANISM: Artificial Sequence
<220> FEATURE:
<223> OTHER INFORMATION: chemically synthesized linker

<400> SEQUENCE: 40

```
Met Gly Gly Ser Ala Thr Gly Ile Phe Asp
 1               5                  10
```

<210> SEQ ID NO 41
<211> LENGTH: 9
<212> TYPE: PRT
<213> ORGANISM: Artificial Sequence
<220> FEATURE:
<223> OTHER INFORMATION: chemically synthesized linker

<400> SEQUENCE: 41

```
Arg Ile Ile Ile Arg Arg Ile Arg Arg
 1               5
```

```
<210> SEQ ID NO 42
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 42

Ala Cys Ser Gly Gly Gly
 1               5

<210> SEQ ID NO 43
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 43

Ser Ala Gly Cys Gly Gly
 1               5

<210> SEQ ID NO 44
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 44

Gly Gly Gly Cys Cys Gly
 1               5

<210> SEQ ID NO 45
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 45

Gly Ser Gly Gly Cys Gly
 1               5

<210> SEQ ID NO 46
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 46

Asp Thr Ala Gly Cys Gly
 1               5

<210> SEQ ID NO 47
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 47

Gly Asp Cys Gly Gly Gly
 1               5
```

```
<210> SEQ ID NO 48
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 48

Gly Cys Ser Gly Ala Gly
1               5

<210> SEQ ID NO 49
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 49

Gly Gly Asp Gly Cys Gly
1               5

<210> SEQ ID NO 50
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 50

Ser Ser Asn Ser Cys Gly
1               5

<210> SEQ ID NO 51
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 51

Ser Asp Cys Ala Tyr Gly
1               5

<210> SEQ ID NO 52
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 52

Asp Thr Asn Cys Gly Gly
1               5

<210> SEQ ID NO 53
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 53

Gly Ser Gly Cys Ser Gly
1               5

<210> SEQ ID NO 54
```

```
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 54

Gly Cys Gly Cys Gly Gly
1               5

<210> SEQ ID NO 55
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 55

Ala Asn Ala Cys Gly Gly
1               5

<210> SEQ ID NO 56
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 56

Gly Gly Ala Cys Gly Gly
1               5

<210> SEQ ID NO 57
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 57

Gly Asn Cys Gly Gly Gly
1               5

<210> SEQ ID NO 58
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 58

Cys Gly Gly Ser Cys Gly
1               5

<210> SEQ ID NO 59
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 59

Gly Ser Thr Ser Cys Gly
1               5

<210> SEQ ID NO 60
<211> LENGTH: 6
```

```
<212> TYPE: PRT
<213> ORGANISM: Artificial Sequence
<220> FEATURE:
<223> OTHER INFORMATION: chemically synthesized linker

<400> SEQUENCE: 60

Asp Gly Gly Cys Ser Gly
1               5

<210> SEQ ID NO 61
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 61

Ala Thr Ser Cys Gly Gly
1               5

<210> SEQ ID NO 62
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 62

Ala Ser Cys Gly Tyr Gly
1               5

<210> SEQ ID NO 63
<211> LENGTH: 6
<212> TYPE: PRT
<213> ORGANISM: Artificial Sequence
<220> FEATURE:
<223> OTHER INFORMATION: chemically synthesized linker

<400> SEQUENCE: 63

Asp Gly Ala Cys Gly Gly
1               5

<210> SEQ ID NO 64
<211> LENGTH: 5
<212> TYPE: PRT
<213> ORGANISM: Artificial Sequence
<220> FEATURE:
<223> OTHER INFORMATION: chemically synthesized linker
<220> FEATURE:
<221> NAME/KEY: VARIANT
<222> LOCATION: 1
<223> OTHER INFORMATION: Xaa = any appended amino acid sequence except
      methionine residue

<400> SEQUENCE: 64

Xaa Gly Ile Phe Asp
1               5

<210> SEQ ID NO 65
<211> LENGTH: 11
<212> TYPE: PRT
<213> ORGANISM: Artificial Sequence
<220> FEATURE:
<223> OTHER INFORMATION: chemically synthesized linker

<400> SEQUENCE: 65

Arg Arg Asp Arg Gly His His His His His
1               5                   10
```

```
<210> SEQ ID NO 66
<211> LENGTH: 6
<212> TYPE: PRT
<213> ORGANISM: Artificial Sequence
<220> FEATURE:
<223> OTHER INFORMATION: chemically synthesized linker
<220> FEATURE:
<221> NAME/KEY: VARIANT
<222> LOCATION: 6
<223> OTHER INFORMATION: Xaa = any appended amino acid sequence except
      his his his his his his (6 x his)

<400> SEQUENCE: 66

Arg Arg Asp Arg Gly Xaa
 1               5

<210> SEQ ID NO 67
<211> LENGTH: 8
<212> TYPE: PRT
<213> ORGANISM: Artificial Sequence
<220> FEATURE:
<223> OTHER INFORMATION: chemically synthesized linker

<400> SEQUENCE: 67

Met Gly His His His His His His
 1               5

<210> SEQ ID NO 68
<211> LENGTH: 16
<212> TYPE: PRT
<213> ORGANISM: Artificial Sequence
<220> FEATURE:
<223> OTHER INFORMATION: chemically synthesized linker

<400> SEQUENCE: 68

Met Gly His His His His His His Gly Gly Ser Gly Ser Gly Ser Gly
 1               5                  10                  15

<210> SEQ ID NO 69
<211> LENGTH: 14
<212> TYPE: PRT
<213> ORGANISM: Artificial Sequence
<220> FEATURE:
<223> OTHER INFORMATION: chemically synthesized linker

<400> SEQUENCE: 69

Gly Gly Ser Gly Ser Gly Ser Gly His His His His His His
 1               5                  10

<210> SEQ ID NO 70
<211> LENGTH: 23
<212> TYPE: PRT
<213> ORGANISM: Artificial Sequence
<220> FEATURE:
<223> OTHER INFORMATION: chemically synthesized linker

<400> SEQUENCE: 70

His His His His His His Ser Arg Ala Trp Arg His Pro Gln Phe Gly
 1               5                  10                  15

Gly His His His His His His
             20

<210> SEQ ID NO 71
<211> LENGTH: 48
<212> TYPE: PRT
<213> ORGANISM: Artificial Sequence
```

```
<220> FEATURE:
<223> OTHER INFORMATION: chemically synthesized linker

<400> SEQUENCE: 71

Gly Gly Gly Ser Gly Gly Gly Ser Gly Gly Thr Gly Gly Gly Ser
 1               5                  10                  15

Gly Gly Gly Arg Arg Ala Asp Ala Ala His His His His His Ser
            20                  25                  30

Arg Ala Trp Arg His Pro Gln Phe Gly Gly His His His His His
        35                  40                  45

<210> SEQ ID NO 72
<211> LENGTH: 18
<212> TYPE: PRT
<213> ORGANISM: Artificial Sequence
<220> FEATURE:
<223> OTHER INFORMATION: chemically synthesized linker

<400> SEQUENCE: 72

His His His His His His Arg Ala Phe Ile Ala Ser Arg Arg Ile Arg
 1               5                  10                  15

Arg Pro

<210> SEQ ID NO 73
<211> LENGTH: 15
<212> TYPE: PRT
<213> ORGANISM: Artificial Sequence
<220> FEATURE:
<223> OTHER INFORMATION: chemically synthesized linker

<400> SEQUENCE: 73

His His His His His His Arg Leu Leu Leu Arg Arg Leu Arg Arg
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: chemically synthesized linker

<400> SEQUENCE: 74

His His His His His His Arg Ile Ile Ile Arg Arg Ile Arg Arg
 1               5                  10                  15

<210> SEQ ID NO 75
<211> LENGTH: 26
<212> TYPE: PRT
<213> ORGANISM: Artificial Sequence
<220> FEATURE:
<223> OTHER INFORMATION: chemically synthesized linker

<400> SEQUENCE: 75

Ala Ala Ser His His His His His His Ser His Arg Ala Thr Pro Asn
 1               5                  10                  15

Thr Ser Pro His His His His His His
            20                  25

<210> SEQ ID NO 76
<211> LENGTH: 26
<212> TYPE: PRT
<213> ORGANISM: Artificial Sequence
<220> FEATURE:
<223> OTHER INFORMATION: chemically synthesized linker
```

```
<400> SEQUENCE: 76

Asn Asp Asn His His His His His His Pro Ser Asn Thr Asn His Asn
1               5                   10                  15

Ser Asn Ser Asn His His His His His
            20              25
```

DEVELOPMENT AND USE OF FLUORESCENT PROBES OF UNBOUND BILIRUBIN

CROSS-REFERENCE TO RELATED APPLICATIONS

This application is the US National Phase under 35 U.S.C. §371 of International Application PCT/US 2012/052395, filed Aug. 24, 2012 which claims priority to U.S. Provisional Application No. 61/527,849, filed Aug. 26, 2011, which is incorporated into PCT/US 2012/052395 by reference.

STATEMENT REGARDING FEDERALLY SPONSORED R&D

This work was supported in part by Roadmap Grant No. R33 DK070314 and SBIR Grant No. R44 DK073535 from the National Institute of Health. Consequently, the U.S. government may have certain rights to this invention.

REFERENCE TO SEQUENCE LISTING

This application incorporates by reference the replacement sequence listing submitted as ASCII text filed via EFS-Web on Oct. 27, 2014. The Sequence Listing is provided as a file entitled "SEQLIST_rev20141027_FFASC.073NP.txt," created on Oct. 27, 2014, and which is approximately 11 kilobytes in size.

FIELD OF THE INVENTION

The field of the invention relates to the identification and use of probes of unbound bilirubin which are fluorescently labeled proteins that undergo a change in fluorescence upon binding bilirubin and which probes are used to measure levels of unbound bilirubin. These probes do not significantly bind or undergo a significant fluorescent change in the presence of other analytes generally present in fluids in which unbound bilirubin levels are determined. These probes of unbound bilirubin can be used in the diagnosis and treatment of hyperbilirubinemia and diseases that result in hyperbilirubinemia.

BACKGROUND OF THE INVENTION

Bilirubin is a product of hemoglobin turnover that is poorly soluble in water and is therefore largely associated with albumin in plasma. A small fraction of the total plasma bilirubin however is soluble in the aqueous phase. This unbound or free fraction is able to permeate the blood brain barrier and, at elevated levels, is neurotoxic [Ahlfors C E, Wennberg R P, Ostrow J D and Tiribelli C. Unbound (free) bilirubin: improving the paradigm for evaluating neonatal jaundice. Clin Chem 55: 1288-1299, 2009]. Under normal conditions total serum bilirubin is maintained at low levels by a regulated balance between production and excretion of bilirubin. However in newborns the mechanisms of regulation may not be sufficiently matured so that the production-excretion balance often favors accumulation, giving rise to the yellow color of jaundice in about 60% of newborns [Maisels M J and McDonagh A F. Phototherapy for neonatal jaundice. N Engl J Med 358: 920-928, 2008]. In most cases this imbalance is benign or may in fact be beneficial for most newborns resolves spontaneously [Wennberg R P, Ahlfors C E, Bhutani V K, Johnson L H and Shapiro S M. Toward understanding kernicterus: a challenge to improve the management of jaundiced newborns. Pediatrics 117: 474-485, 2006; Gopinathan V, Miller N J, Milner A D and Rice-Evans C A. Bilirubin and ascorbate antioxidant activity in neonatal plasma. FEBS Lett 349: 197-200, 1994]. Concentrations of unbound bilirubin can however rise to levels that are neurotoxic, resulting in deficits ranging from reversible hearing defects to the more severe neurological sequelae of kernicterus that in rare instances include death [Ahlfors C E, Wennberg R P, Ostrow J D and Tiribelli C. Unbound (free) bilirubin: improving the paradigm for evaluating neonatal jaundice. Clin Chem 55: 1288-1299, 2009].

Early intervention using phototherapy or exchange transfusion can treat bilirubin mediated neurotoxicity in neonates [Maisels M J and McDonagh A F. Phototherapy for neonatal jaundice. N Engl J Med 358: 920-928, 2008; Morris B H, Oh W, Tyson J E, Stevenson D K, Phelps D L, O'Shea T M, McDavid G E, Perritt R L, Van Meurs K P, Vohr B R, Grisby C, Yao Q, Pedroza C, Das A, Poole W K, Carlo W A, Duara S, Laptook A R, Salhab W A, Shankaran S, Poindexter B B, Fanaroff A A, Walsh M C, Rasmussen M R, Stoll B J, Cotten C M, Donovan E F, Ehrenkranz R A, Guillet R and Higgins R D. Aggressive vs. conservative phototherapy for infants with extremely low birth weight. N Engl J Med 359: 1885-1896, 2008; Kuzniewicz M W, Escobar G J and Newman T B Impact of universal bilirubin screening on severe hyperbilirubinemia and phototherapy use. Pediatrics 124: 1031-1039, 2009]. Guidelines for intervention depend principally on total bilirubin levels, with account taken for gestational age and risk factors [Bhutani V K, Johnson L and Sivieri E M. Predictive ability of a predischarge hour-specific serum bilirubin for subsequent significant hyperbilirubinemia in healthy term and near-term newborns. Pediatrics 103: 6-14, 1999]. However fundamental biochemical and increasing clinical evidence predicts that unbound bilirubin rather than total bilirubin should more accurately correlate with bilirubin mediated neurotoxicity [Ahlfors C E, Wennberg R P, Ostrow J D and Tiribelli C. Unbound (free) bilirubin: improving the paradigm for evaluating neonatal jaundice. Clin Chem 55: 1288-1299, 2009; Wennberg R P, Ahlfors C E and Aravkin A Y. Intervention guidelines for neonatal hyperbilirubinemia: an evidence based quagmire. Curr Pharm Des 15: 2939-2945, 2009; Ahlfors C E, Amin S B and Parker A E. Unbound bilirubin predicts abnormal automated auditory brainstem response in a diverse newborn population. J Perinatol 29: 305-309, 2009; Oh W, Stevenson D K, Tyson J E, Morris B H, Ahlfors C E, Bender G J, Wong R J, Perritt R, Vohr B R, Van Meurs K P, Vreman H J, Das A, Phelps D L, O'Shea T M and Higgins R D. Influence of clinical status on the association between plasma total and unbound bilirubin and death or adverse neurodevelopmental outcomes in extremely low birth weight infants. Acta Paediatr 99: 673-678, 2010]. Therefore unbound bilirubin should be superior to total bilirubin for identifying neonates at risk for bilirubin neurotoxicity [Ahlfors C E. Predicting bilirubin neurotoxicity in jaundiced newborns. Curr Opin Pediatr 22: 129-133, 2010].

Aggressive phototherapy in premature infants is designed to maintain total bilirubin below 5 mg/dL [Morris B H, Oh W, Tyson J E, Stevenson D K, Phelps D L, O'Shea T M, McDavid G E, Perritt R L, Van Meurs K P, Vohr B R, Grisby C, Yao Q, Pedroza C, Das A, Poole W K, Carlo W A, Duara S, Laptook A R, Salhab W A, Shankaran S, Poindexter B B, Fanaroff A A, Walsh M C, Rasmussen M R, Stoll B J, Cotten C M, Donovan E F, Ehrenkranz R A, Guillet R and Higgins R D. Aggressive vs. conservative phototherapy for infants with extremely low birth weight. N Engl J Med 359:

1885-1896, 2008]. However Morris et al found no difference in outcome (death and neurologic development impairment) for patients treated to maintain total bilirubin at less than 5 mg/dL and those maintained at less than 8 mg/dL. However a follow up study by these investigators found that outcomes were well correlated with unbound bilirubin but not total bilirubin [Oh W, Stevenson D K, Tyson J E, Morris B H, Ahlfors C E, Bender G J, Wong R J, Perritt R, Vohr B R, Van Meurs K P, Vreman H J, Das A, Phelps D L, O'Shea T M and Higgins R D. Influence of clinical status on the association between plasma total and unbound bilirubin and death or adverse neurodevelopmental outcomes in extremely low birth weight infants. *Acta Paediatr* 99: 673-678, 2010]. This suggests that using total bilirubin for determining when to deliver phototherapy may have been misleading because the levels of total bilirubin were not coupled to unbound bilirubin, the toxic fraction of bilirubin. Decoupling of total bilirubin and unbound bilirubin may result from the presence of molecules that interfere significantly with bilirubin binding to albumin. For example, even if total bilirubin was as low as 1 mg/dL, displacement of just 0.2% of total bilirubin by interfering molecules would result in unbound bilirubin=34 nM. This is an unbound bilirubin level that exceeds that thought to be toxic for term newborns and it is generally thought that much lower unbound bilirubin levels would be toxic for premature infants such as those in the Morris et al trial [Morris B H, Oh W, Tyson J E, Stevenson D K, Phelps D L, O'Shea T M, McDavid G E, Perritt R L, Van Meurs K P, Vohr B R, Grisby C, Yao Q, Pedroza C, Das A, Poole W K, Carlo W A, Duara S, Laptook A R, Salhab W A, Shankaran S, Poindexter B B, Fanaroff A A, Walsh M C, Rasmussen M R, Stoll B J, Cotten C M, Donovan E F, Ehrenkranz R A, Guillet R and Higgins R D. Aggressive vs. conservative phototherapy for infants with extremely low birth weight. *N Engl J Med* 359: 1885-1896, 2008].

Many drugs and metabolites can bind to albumin and as a result, bilirubin is displaced from its bound state on albumin and thereby the unbound concentration of bilirubin is increased whether or not the total bilirubin concentration increases [Spear M L, Stahl G E, Paul M H, Egler J M, Pereira G R and Polin R A. The effect of 15-hour fat infusions of varying dosage on bilirubin binding to albumin. *JPEN J Parenter Enteral Nutr* 9: 144-147, 1985; Amin S B. Effect of free fatty acids on bilirubin-albumin binding affinity and unbound bilirubin in premature infants. *JPEN J Parenter Enteral Nutr* 34: 414-420, 2010]. Especially important bilirubin displacing metabolites are free fatty acids (FFA). FFA are always present but are maintained at low levels and do not have a significant effect on healthy term newborns. However under conditions of stress, as for example due to sepsis, FFA levels can increases significantly [Nogueira A C, Kawabata V, Biselli P, Lins M H, Valeri C, Seckler M, Hoshino W, Junior L G, Bernik M M, de Andrade Machado J B, Martinez M B, Lotufo P A, Caldini E G, Martins E, Curi R and Soriano F G. Changes in plasma free fatty acid levels in septic patients are associated with cardiac damage and reduction in heart rate variability. *Shock* 29: 342-348, 2008]. In addition to disease and stress preterm infants in the NICU can produce extremely large increases in FFA levels as a consequence of receiving by parenteral nutrition an oil emulsion such as Intralipid® [Spear M L, Stahl G E, Paul M H, Egler J M, Pereira G R and Polin R A. The effect of 15-hour fat infusions of varying dosage on bilirubin binding to albumin. *JPEN J Parenter Enteral Nutr* 9: 144-147, 1985; Amin S B. Effect of free fatty acids on bilirubin-albumin binding affinity and unbound bilirubin in premature infants. *JPEN J Parenter Enteral Nutr* 34: 414-420, 2010]. FFA bind albumin with high affinities similar to bilirubin. Unlike bilirubin, FFA have multiple high affinity binding sites so that only when an appreciable fraction of the albumin binding sites are occupied by FFA does bilirubin displacement become significant [Spear M L, Stahl G E, Paul M H, Egler J M, Pereira G R and Polin R A. The effect of 15-hour fat infusions of varying dosage on bilirubin binding to albumin. *JPEN J Parenter Enteral Nutr* 9: 144-147, 1985; Amin S B. Effect of free fatty acids on bilirubin-albumin binding affinity and unbound bilirubin in premature infants. *JPEN J Parenter Enteral Nutr* 34: 414-420, 2010]. Which newborns receiving Intralipid® will produce large enough quantities of FFA cannot be easily predicted because it depends on gestational age and likely on factors such as enzymatic activity, adiposity and others [Spear M L, Stahl G E, Paul M H, Egler J M, Pereira G R and Polin R A. The effect of 15-hour fat infusions of varying dosage on bilirubin binding to albumin. *JPEN J Parenter Enteral Nutr* 9: 144-147, 1985; Amin S B. Effect of free fatty acids on bilirubin-albumin binding affinity and unbound bilirubin in premature infants. *JPEN J Parenter Enteral Nutr* 34: 414-420, 2010]. It is critical to monitor the unbound concentration of FFA (FFAu) during lipid infusion because elevated FFAu levels can cause immune suppression, cardiac damage and reduction in heart rate variability, and elevated levels of unbound bilirubin. In addition, because the unbound levels of these metabolites are dependent upon many patient-specific factors, only by directly monitoring unbound bilirubin during Intralipid® infusion can those infants at risk for bilirubin neurotoxicity be identified. This is particularly true for bilirubin because the elevated plasma levels of FFA caused by increasing Intralipid® concentrations produce elevated unbound bilirubin concentrations without changing the total bilirubin concentration.

Intracellular lipid binding proteins (iLBP) are a family of low-molecular weight single chain polypeptides. There are four recognized subfamilies. Subfamily I contains proteins specific for vitamin A derivatives such as retinoic acid and retinol. Subfamily II contains proteins with specificities for bile acids, eicosanoids, and heme. Subfamily III contains intestinal type fatty acid binding proteins (FABPs) and Subfamily IV contains all other types of fatty acid binding protein [Haunerland N H and Spener F. Fatty acid-binding proteins—insights from genetic manipulations. *Prog Lipid Res* 43: 328-349, 2004] including an FABP that binds bilirubin with low affinity [Di Pietro S M and Santome J A. Isolation, characterization and binding properties of two rat liver fatty acid-binding protein isoforms. *Biochim Biophys Acta* 1478: 186-200, 2000]. The entire family is characterized by a common 3-dimensional fold. Ligand binding properties of the different subfamilies overlap considerably. The wild type proteins of subfamily I [Richieri G V, Ogata R T, Zimmerman A W, Veerkamp J H and Kleinfeld A M. Fatty acid binding proteins from different tissues show distinct patterns of fatty acid interactions. *Biochemistry* 39: 7197-7204, 2000] and subfamily II both bind fatty acids as well as their native ligands. Moreover, single amino acid substitutions are able to interconvert the ligand binding properties of proteins of subfamilies I and II [Jakoby M G, Miller K R, Toner J J, Bauman A, Cheng. L, Li E and Cistola D P. Ligand-protein electrostatic interactions govern the specificity of retinol- and fatty acid-binding proteins. *Biochemistry* 32: 872-878, 1993].

U.S. Pat. No. 5,470,714, U.S. Pat. No. 6,444,432, U.S. Pat. No. 7,601,510 and U.S. publication 2010/0298162 which are incorporated herein by reference, describe methods for generating probes and the probes for the determination of unbound analytes. These probes were constructed using either native or mutant forms of proteins from the iLBP family. As discussed above, this family includes FABPs [Banaszak L, Winter N, Xu Z, Bernlohr D A, Cowan S and Jones T A. Lipid-binding proteins A family of fatty acid and retinoid transport proteins. *Adv Protein Chem* 45: 89-151, 1994; Bernlohr D A, Simpson M A, Hertzel A V and Banaszak L J. Intracellular lipid-binding proteins and their genes. *Annu Rev Nutr* 17: 277-303, 1997]. FABPs are intracellular proteins of approximately 15 kDa molecular weight and have a binding site that in the wild type proteins binds 1 or 2 FFA as well as other metabolites.

SUMMARY OF THE INVENTION

Embodiments of the invention are directed to the identification of probes that are highly specific for unbound bilirubin and the methods for using these probes for determining unbound bilirubin concentrations in samples ranging from simple aqueous solutions to complex biological samples including human fluids (blood, csf, urine, interstitial) which includes one or more of the following steps:

generating the probes using the methods of U.S. Pat. No. 7,601,510 and US publication 2010/0298162 and the method of generating ratio bilirubin probes by use of a second free fluorophore or a second fluorophore attached to or embedded in a solid substrate or polymer, such as a protein, polydextran, or polystyrene, for example, and calibrating the probes to determine the dissociation constant using equations (1 to 3), identifying methods for linking probes to solid substrates and describing properties of such probes in devices and describing methods for accurate and precise determination of unbound bilirubin levels in such devices [properties to be determined include: effects of probe dissociation, albumin buffering, bilirubin binding to bead not probe, equilibrium rates on beads compared to solution, relationship of solution to solid measurements], refining bilirubin probe specificity by a combination of testing in defined aqueous solutions against a panel of potential interferants including common metabolites, drugs, bilirubin photoisomers and conjugated bilirubin and further mutations to achieve specificity consistent with other analyte contributions equivalent to less than 1 nM unbound bilirubin or some medically suitable level, testing quantitation by measurement of unbound bilirubin in defined human plasma spiked with bilirubin to ensure specificity for unbound bilirubin in human blood samples, using probes in solution or bound to solid surfaces and calculating unbound bilirubin concentrations as described in equations (4 and 5).

Preferred embodiments are directed to probes based upon an iLBP, such as the lipid binding protein which corresponds to SEQ ID NO: 3 which includes one or more amino acid substitutions and a fluorophore. Preferably, the fluorophore is attached to a lysine residue, the N-terminus amino group of the iLBP, or to a cysteine substitution. Preferably, the probe binds to bilirubin but does not significantly bind to fatty acid.

In a preferred embodiment, the probe includes substitutions 14R, 18L, 25C, 27A, 38V, 60R, 73F, 106L, 115R, 117D, optionally in combination with Rhodamine B (BL22P1B11; SEQ ID NO: 35).

In another preferred embodiment, the probe includes substitutions 14R, 18L, 38V, 60R, 73F, 106C, 115R and 117D, optionally in combination with Rhodamine B (L24P19C7; SEQ ID NO: 36).

In preferred embodiments, the probe corresponds to the lipid binding protein of SEQ ID NO: 3 with one or more amino acid substitutions at positions selected from 14, 18, 23, 25, 27, 31, 36, 38, 55, 60, 72, 73, 74, 78, 102, 104, 106, 115 and 117.

In some preferred embodiments, the fluorophore is attached to a cysteine substitution at positions 22, 24, 25, 26, 27, 29, 30, 33, 54, 74, 76, 97 or 98.

In some preferred embodiments, the fluorophore is attached to a lysine substitution at positions 22, 24, 25, 26, 27, 29, 30, 33, 54, 74, 76, 97 or 98.

In some preferred embodiments, the probe is substituted at positions 7R 20R 46R 100R 125R and 130R (KR6), more preferably, 7R 16R 20R 29R 37R 46R 50R 88R 92R 94R 100R 125R 129R and 130R (KR14).

In preferred embodiments, the probe includes least one linker. The linker(s) may be one or more selected from ACSGGG (SEQ ID NO: 42), SAGCGG (SEQ ID NO: 43), GGGCCG (SEQ ID NO: 44), GSGGCG (SEQ ID NO: 45), DTAGCG (SEQ ID NO: 46), GDCGGG (SEQ ID NO: 47), GCSGAG (SEQ ID NO: 48), GGDGCG (SEQ ID NO: 49), SSNSCG (SEQ ID NO: 50), SDCAYG (SEQ ID NO: 51), DTNCGG (SEQ ID NO: 52), GSGCSG (SEQ ID NO: 53), GCGCGG (SEQ ID NO: 54), ANACGG (SEQ ID NO: 55), GGACGG (SEQ ID NO: 56), GNCGGG (SEQ ID NO: 57), CGGSCG (SEQ ID NO: 58), GSTSCG (SEQ ID NO: 59), DGGCSG (SEQ ID NO: 60), ATSCGG (SEQ ID NO: 61), ASCGYG (SEQ ID NO: 62), DGACGG (SEQ ID NO: 63), GGSGSGSGG (SEQ ID NO: 26), GGGSGGGSGGGTGGGSGGGRRADAA (SEQ ID NO: 27), SRAWRHPQFGG (SEQ ID NO: 28), RAFIASRRIRRP (SEQ ID NO: 29), RLLLRRLRR (SEQ ID NO: 30), RIIIRRIRR (SEQ ID NO: 41), AAS, NDN, PSNTNHNSNSN (SEQ ID NO: 31), SHRATPNTSPH (SEQ ID NO: 32) and combinations thereof Preferably, a polynucleotide template encodes iLBP muteins having a cleavable or noncleavable affinity tag. More preferably, the template polynucleotide template encodes iLBP muteins having a poly-histidine affinity tag and the solid matrix includes an immobilized metal chelate.

In preferred embodiments, the iLBP muteins are labeled with a single fluorophore at a pH of less than 8 so that the fluorophore preferentially reacts with the cysteine sidechain. Preferably, the fluorophore is acrylodan, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas Red, C5-Bromoacetamide, Alexa Fluor 750 C5-maleimide, or BODIPY 577/618.

In second preferred embodiments, the iLBP muteins are labeled with a single fluorophore at a pH of greater than 8 so that the fluorophore preferentially reacts with an amine, such as the protein amino terminus or a lysine sidechain. Preferably, the fluorophore is acrylodan or a longer wavelength absorbing and emitting fluorophore such as Alexa Fluor dyes, Bodipy dyes, fluorescein derivatives, rhodamine derivatives, Texas Red, Biotium CF750 SE, Kodak X-Sight 670 LSS dye, LiCor IRDye 680 LT or LiCor IRDye 700DX.

In alternate preferred embodiments, the iLBP muteins are labeled with a first fluorophore and a second fluorophore. Preferably, the one fluorophore is acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino-7-nitrobenz-2-oxa-1,3-diazole (IANBDA). Preferably, the other fluorophore is a longer wavelength absorbing and emitting fluorophore such as Alexa Fluor dyes, Bodipy, fluorescein derivatives, rhodamine derivatives or Texas Red. In some preferred embodiments, labeling includes reacting cysteine with the first fluorophore at pH less than or equal to 8; and reacting lysine with the second fluorophore at pH greater than 8. In other preferred embodiments, labeling includes reacting cysteine with the first fluorophore at pH less than or equal to 8; and reacting the amino terminus of the iLBP mutein with the second fluorophore at pH greater than 8.

In some embodiments of the invention, a second fluorophore is provided by addition of an acceptor protein or peptide domain to each of the iLBP muteins. Preferably, the acceptor protein or peptide domain is selected from SNAP-tag, CLIP-tag and ACP-tag and the like. In some embodiments, the polynucleotide mutants in the library contain a nucleotide segment encoding a fluorescent protein. Preferably, the acceptor protein domain or the fluorescent protein has zero or a significantly reduced response in intensity and/or wavelength of emitted fluorescence upon exposure to bilirubin compared to the fluorescence of the iLBP mutein portion of the probe.

In some embodiments, the first fluorophore is attached to a lysine substitution and the second fluorophore is attached to a cysteine substitution which is selected from positions 22, 24, 25, 26, 27, 29, 30, 33, 54, 74, 76, 97 or 98.

Embodiments of the invention are directed to compositions having an iLBP mutein labeled with a first fluorophore and a second fluorophore. Preferably, the second fluorophore is free in solution or attached to a protein which does not bind bilirubin. Preferably, the first fluorophore and the second fluorophore are capable of excitation at the same wavelength and the emission wavelength of the first fluorophore and the second fluorophore are different. Preferably, the second fluorophore is not affected (does not change its emission) in response to bilirubin binding to the iLBP mutein. Preferably, the first fluorophore is acrylodan and the second fluorophore is selected from Rhodamine B, NBD, Lucifer yellow, Texas Red, a Bodipy dye and an Alexa Fluor dye. More preferably, the first fluorophore is LiCor 700DX and the second fluorophore is, for example, Texas Red or an Alexa fluor dye, or a Bodipy dye.

In preferred embodiments, a change in ratio of fluorescence index is measured at two different wavelengths and used to determine the unbound bilirubin concentration.

In preferred embodiments, the emission intensity of the fluorophore(s) attached to the probes described herein is not affected by the absorbance of blood components such as bilirubin and hemoglobin.

In some embodiments, the first fluorophore is attached to a cysteine and is selected from acrylodan, danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA) and the second fluorophore is selected from Alexa Fluor dyes, Bodipy, fluorescein derivatives, rhodamine derivatives and Texas Red.

In some embodiments, the first fluorophore is attached to a lysine and is selected from acrylodan, Biotium CF750SE, Kodak X-Sight 670 LSS dye, Licor IR Dye 680 LT and Licor IR Dye 700DX and the second fluorophore is selected from Alexa Fluor dyes, Bodipy, fluorescein derivatives, rhodamine derivatives and Texas Red.

In other preferred embodiments of the invention described here a second different fluorophore is provided as a soluble molecule free in solution. Such a probe responds to bilirubin binding to the protein portion of the probe with a change in the ratio of a fluorescence index measured at two different wavelengths. This allows probes that do not reveal a ratio fluorescence index change in response to bilirubin binding to be converted readily into a ratio probe by using a second but unattached fluorophore that reveals no significant response to bilirubin. The second free fluorophore can have a longer or shorter emission wave length than the first (protein bound) fluorophore but both fluorophores must have a common excitation wave length. For example in some embodiments the first (protein linked) fluorophore is acrylodan and examples of the second include but are not limited to Rhodamine B, NBD, Lucifer yellow and Texas Red either free in solution or attached to or embedded in another polymer or solid substrate. This arrangement has the advantage that the concentration of the free fluorophore can be adjusted so that emission intensities of both fluorophores are similar even when the maximum excitation wavelength for the second fluorophore is different than for the first fluorophore. This type of ratio probe using a second different fluorophore not attached to the probe eliminates the problem of energy transfer quenching of one of the two fluorophores by the other, typically when both fluorophores are located on the same macromolecule such as a protein.

In some embodiments, the second fluorophore is attached to an acceptor protein or peptide domain on the probe. Preferably, the acceptor protein or peptide domain is selected from SNAP-tag, CLIP-tag, and ACP-tag. Preferably, the probe includes substitutions 7R 20R 46R 100R 125R and 130R (KR6). More preferably, the probe includes substitutions 7R 16R 20R 29R 37R 46R 50R 88R 92R 94R 100R 125R 129R and 130R (KR14).

In some embodiments, for any of the probes described above the N terminus AFD may be substituted with MGIFD (SEQ ID NO: 38), MGCFD (SEQ ID NO: 39) or MGGSATGIFD (SEQ ID NO: 40), for example.

In some embodiments, the probe includes at least one linker such as ACSGGG (SEQ ID NO: 42), SAGCGG (SEQ ID NO: 43), GGGCCG (SEQ ID NO: 44), GSGGCG (SEQ ID NO: 45), DTAGCG (SEQ ID NO: 46), GDCGGG (SEQ ID NO: 47), GCSGAG (SEQ ID NO: 48), GGDGCG (SEQ ID NO: 49), SSNSCG (SEQ ID NO: 50), SDCAYG (SEQ ID NO: 51), DTNCGG (SEQ ID NO: 52), GSGCSG (SEQ ID NO: 53), GCGCGG (SEQ ID NO: 54), ANACGG (SEQ ID NO: 55), GGACGG (SEQ ID NO: 56), GNCGGG (SEQ ID NO: 57), CGGSCG (SEQ ID NO: 58), GSTSCG (SEQ ID NO: 59), DGGCSG (SEQ ID NO: 60), ATSCGG (SEQ ID NO: 61), ASCGYG (SEQ ID NO: 62), DGACGG (SEQ ID NO: 63), GGSGSGSGG (SEQ ID NO: 26), GGGSGGGSGGGTGGGSGGGRRADAA (SEQ ID NO: 27), SRAWRHPQFGG (SEQ ID NO: 28), RAFIASRRIRRP (SEQ ID NO: 29), RLLLRRLRR (SEQ ID NO: 30), RIIIRRIRR (SEQ ID NO: 41), AAS, NDN, PSNTNHNSNSN (SEQ ID NO: 31), SHRATPNTSPH (SEQ ID NO: 32) or combinations thereof.

Embodiments of the invention are directed to probes in which the fluorophore is attached to a cysteine residue. Preferably, the fluorophore is selected from acrylodan, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), Texas Red C2-Maleimide, Lucifer yellow iodoacetamide, Alexafluor 680 maleimide, Kodak X-Sight 670 LSS dye, Texas red C2-maleimide, Texas Red C5-Bromoacetamide, Alexa Fluor 750 C5-maleimide, and BODIPY 577/618.

Embodiments of the invention are directed to probes in which the fluorophore is attached to a lysine residue. Preferably, the fluorophore is selected from of acrylodan, Alexa Fluor dyes, Bodipy, fluorescein derivatives, rhodamine derivatives, Texas Red, Biotium CF750 SE, Kodak X-Sight 670 LSS dye, LiCor IRDye 680 LT, and LiCor IRDye 700DX.

In some embodiments, any of the probes as described above may include two or more tags at the C or N-terminus of the probe in combination with one or more linkers for attachment to a solid support.

In preferred embodiments, the probe includes a lysine at position 25 labeled with LI-COR 700DX.

In some preferred embodiments, the probe is attached to a solid support using two His-tags and two linkers.

In some preferred embodiments, the probe includes one or more tags, preferably selected from his-tag and PS-tags.

Embodiments of the invention are directed to compositions which contain one or more probe as described above.

Other preferred embodiments include bilirubin probes that are attached to solid substrates that include but are not limited to polystyrene or latex beads and which beads can be immobilized on a surface. Examples of the use of such immobilized particles include but are not limited to adhered to the bottom surface of multi-well plates for high-throughput measurements or in channels of disposable microfluidics devices. Examples of bilirubin probes that are designed to be immobilized on surfaces include ones that are linked through chemical reaction with either cysteine or lysine (first two groups of Table 8) to appropriate groups on the solid support surface as well as those linked through non-covalent interactions (the third group of Table 8 and examples 6 and 7). Additionally a second fluorophore can be attached or embedded within the solid support surface thereby separating the two fluorophores so as to eliminate energy transfer and thereby obtain a ratio response to bilirubin binding. Additionally a second fluorophore can be attached to another protein, such as an iLBP, or another type of polymer, such as dextran, that does not bind or is unresponsive to bilirubin.

Embodiments of the invention are directed to a solid substrate which includes any of the probes described above attached to the solid substrate. Preferably, the solid substrate is a polystyrene or latex bead, Ni-agarose bead, optionally with iron core, and/or microfluidic device or multiwell plate. The probes selected for attachment to the solid substrate may contain any of the modifications described above alone or in combination including but not limited to N-terminal modifications, linkers and substitutions of surface lysines (KR6 and KR14).

In preferred embodiments, the probe is tagged for attachment to the solid substrate. In preferred embodiments, the tag includes one or more of His-tag, biotin, Flag-epitope, c-myc epitope, HA-tag, glutathione-S-transferase (GST), maltose binding protein (MBP), a chitin binding domain (CBD), Thioredoxin, β-Galactosidase, VSV-Glycoprotein, calmodulin binding protein, a polystyrene (PS) hydrophobic tag, and a metal affinity tag.

In some embodiments, the solid substrate includes a second fluorophore. The second fluorophore may be attached to a protein that does not bind bilirubin.

Preferred embodiments are directed to a solid substrate in which the probe has a tag and the solid substrate includes a receptor for the tag. Preferably, the tag is a poly-histidine tag and the solid substrate includes an immobilized metal chelate.

Embodiments of the invention are directed to an iLBP mutein having a single cysteine or lysine labeled with a fluorescent dye. Preferably, any surface lysines or any other cysteines with fluorescent labeling activity under cysteine/lysine-specific labeling conditions are replaced with another amino acid, preferably alanine or arginine. In the preferred embodiment, which utilizes an iLBP mutein template corresponding to SEQ ID NO: 3, the lysine at position 27 is highly reactive and is mutated, typically to alanine.

In preferred embodiments, bilirubin is complexed with a carrier macromolecule such as albumin, lipid binding proteins, lipid vesicles or cyclodextrin. The complex of bilirubin and the carrier macromolecule buffers the concentration of the unbound bilirubin which provides clamping of a level of unbound bilirubin. In preferred embodiments, the carrier macromolecule is albumin. In further preferred embodiments the albumin is human serum albumin which has a larger affinity for bilirubin than, for example, bovine serum albumin and is therefore a more preferred albumin buffer for bilirubin in some embodiments.

In some embodiments the bilirubin absorbance overlaps with the excitation wavelength of the bilirubin probe's fluorophore and the calibration is performed in a cuvette where the path length d is sufficiently large that inner filter absorbance is significant. In this case the emission intensities of the fluorophore must be corrected for inner filter absorbance due to bilirubin absorbance at the excitation wavelength and possibly at the emission wavelength prior to fitting the calibration equation to the bilirubin probe's titration data or when determining the concentration of free (unbound) bilirubin [Bf] with equations 4 or 5. The equation for the corrected emission intensities ($I_{\lambda em}^{Corr}$) is:

$$I_{\lambda em}^{Corr} = I_{\lambda em} 10^{B_T \epsilon(\lambda ex) \frac{d}{2}} \quad (1)$$

where $I_{\lambda em}$ is the measured fluorescence emission intensity at the wavelength $\lambda_{em}$, $B_T$ is the total bilirubin concentration, $\epsilon(\lambda_{ex})$ is the bilirubin extinction coefficient at the excitation or emission wavelength ($\lambda_{ex}$) and d is the cuvette path length. As equation (1) indicates the inner filter correction requires knowledge of the total bilirubin concentration ($B_T$), which must also be measured in order to determine [$B_f$]. The inner filter excitation correction is important for single fluorophore, non-ratio, bilirubin probes for which equation (2) is used for the calibration.

Embodiments of the invention are directed to methods of calibrating the bilirubin probes by mixing the probe with an aqueous sample of bilirubin, measuring the fluorescence, and determining the calibration parameters from the measured fluorescence by fitting with the following equations 1 and 2 or 3:

$$\frac{I_{\lambda em}}{I_o} = 1 - \frac{(K_d + B_t + P_T) - \sqrt{(K_d + B_t + P_T)^2 - 4B_T P_T}}{2P_T} \quad (2)$$

$$R = -\frac{\sqrt{(P_T^2 + (2K_d - 2B_T)P_T + K_d^2 + 2B_T K_d + B_T^2)(rR_o^2 - R_o)} + (P_T + K_d - B_T)rR_o^2 + (-P_T + K_d + B_T)R_o}{2(B_T r^2 R_o^2 - (P_T + K_d + B_T)rR_o + P_T)} \quad (3)$$

where $I_{\lambda em}$ is the fluorescence intensity of the probe in the sample with blank subtracted, $I_o$ is the intensity of the probe in the absence of bilirubin, $P_T$ is the total bilirubin probe concentration, $B_T$ is the total bilirubin concentration, R is the measured fluorescence ratio $((I_{\lambda 1}/I_{\lambda 2})$ where $I_{\lambda 1}$ is the fluorescence intensity from the first fluorophore at wavelength $\lambda 1$ and $I_{\lambda 2}$ is the fluorescence intensity from the second fluorophore at wavelength $\lambda 2$, $R_o$ is the ratio in the absence of bilirubin, r is the $I_{\lambda 2}/I_{\lambda 1}$ ratio of the probe in the absence of the second fluorophore, and $K_d$ is the dissociation constant.

Embodiments of the invention are directed to methods of measuring the concentration of free bilirubin [Bf] by following a combination of the following steps which include optionally measuring the fluorescence of the sample, mixing the probe with a sample, and measuring the fluorescence, optionally, subtracting the sample from probe with sample fluorescence and determining the concentration of [Bf] from the measured fluorescence.

In preferred embodiments, at least one of the following equations 4-6 is used to calibrate the probe and/or measure [Bf]:

$$[B_f] = K_d\left(\frac{I_o}{I_{\lambda em}} - 1\right). \quad (4)$$

$$[B_f] = K_d\left(\frac{(R - R_o)}{(RrR_o - R)}\right) \quad (5)$$

where, $I_{\lambda em}$ is the fluorescence intensity of the probe in the sample with blank subtracted, $I_o$ is the intensity of the probe in the absence of bilirubin, R is the measured fluorescence ratio $((I_{\lambda 1}/I_{\lambda 2})$ where $I_{\lambda 1}$ is the fluorescence intensity from the first fluorophore at wavelength $\lambda 1$ and $I_{\lambda 2}$ is the fluorescence intensity from the second fluorophore at wavelength $\lambda 2$, $R_o$ is the ratio in the absence of bilirubin, r is the $I_{\lambda 2}/I_{\lambda 1}$ ratio of the probe in the absence of the second fluorophore, $K_d$ is the dissociation constant, and Is is the emission intensity at bilirubin saturation of the probe.

In some embodiments, the probe has two fluorophores or a combination of a probe with one fluorophore and a second fluorophore either free in solution or attached to a polymer such as a protein which does not bind bilirubin. In some embodiments a probe with one fluorophore which binds or responds to bilirubin is attached to a solid substrate and a second fluorophore is attached to another protein that is also attached to the solid substrate but that doesn't bind or respond to bilirubin.

In some embodiments, the probe has a single fluorophore and the method includes one or more steps for correcting for inner filter excitation.

In preferred embodiments, the sample comprises a carrier macromolecule for the bilirubin such as albumin, lipid binding proteins, lipid vesicles or cyclodextrin.

In some embodiments, the probe is attached to a solid support. In some preferred embodiments, microfluidics allows measurements of undiluted blood samples.

Preferably, the sample is from a human, an animal or a plant. In preferred embodiments, the sample is from whole blood, blood plasma, blood serum, urine, CSF, saliva, gastric juices, interstitial fluid or lymph. In some embodiments, the sample is from patients receiving intravenous infusion of oil emulsions. In some embodiments, the sample is from patients that may be producing, from disease or stress, molecules that displace bilirubin from albumin. In some embodiments, the sample is from patients that are undergoing phototherapy, transfusion or other therapies that reduce bilirubin levels.

Embodiments of the invention are directed to methods for measuring the concentration of unbound FFA in a blood sample from patients receiving intravenous infusion of an oil emulsion by one or more of the following steps:
  optionally, measuring the fluorescence of the sample
  mixing the sample and an FFAu probe,
  measuring the probe fluorescence, and
  calculating the FFAu concentration.

In some embodiments, the risk of damage to the patient based upon the FFAu concentration is determined and treatment is provided to prevent, treat, or reduce the risk of the damage.

Embodiments of the invention are directed to a kit which may include one or more collection devices for collecting a sample from a patient, one or more probes as described above or a composition containing one or more probes in a suitable carrier, and optionally, a reference standard comprising a known concentration of unbound bilirubin.

Embodiments of the invention are directed to probes as defined in any of Tables 2, 3, 4, 5, 6, 7, 8, and 10.

Embodiments of the invention are directed to methods to determine risk of unbound bilirubin and/or unbound FFA toxicity in patients receiving a fat emulsion (Intralipid®) which includes one or more of the following steps:
  obtaining a sample from the patient, contacting the sample with one or more probes such as ADIFAB2, L19CP10C7, L138P1H8N24C, L22P5E11, L61P8B12, L4BP4B9, and L119P3E5 to determine levels of one or more FFAu,
  determining levels of unbound bilirubin, and
  comparing FFAu and unbound bilirubin levels to levels obtained from a normal population to determine risk of toxicity.

Embodiments of the invention are directed to a solid substrate which includes a probe such as an iLBP, where the lipid binding protein corresponds to SEQ ID NO: 3 having one or more amino acid substitutions and a fluorophore. Preferably, the fluorophore is attached to a lysine residue, the N-terminus amino group of the iLBP, or to a cysteine substitution. Preferably, the probe binds to fatty acid and is attached to the solid substrate, Preferably the solid substrate is a polystyrene or latex bead, Ni-agarose bead, optionally with iron core, microfluidic device, or multiwell plate.

In preferred embodiments, the probe attached to the solid substrate has a modified N terminus in which AFD of the probe is substituted with MGIFD (SEQ ID NO: 38), MGCFD (SEQ ID NO: 39), or MGGSATGIFD (SEQ ID NO: 40).

Preferably, the probe attached to the solid substrates has modifications of surface lysines such as substitutions 7R 20R 46R 100R 125R and 130R (KR6), more preferably substitutions 7R 16R 20R 29R 37R 46R 50R 88R 92R 94R 100R 125R 129R and 130R (KR14).

In preferred embodiments, the probe attached to the solid substrate includes at least one linker such as ACSGGG (SEQ ID NO: 42), SAGCGG (SEQ ID NO: 43), GGGCCG (SEQ ID NO: 44), GSGGCG (SEQ ID NO: 45), DTAGCG (SEQ ID NO: 46), GDCGGG (SEQ ID NO: 47), GCSGAG (SEQ ID NO: 48), GGDGCG (SEQ ID NO: 49), SSNSCG (SEQ ID NO: 50), SDCAYG (SEQ ID NO: 51), DTNCGG (SEQ ID NO: 52), GSGCSG (SEQ ID NO: 53), GCGCGG (SEQ ID NO: 54), ANACGG (SEQ ID NO: 55), GGACGG (SEQ ID NO: 56), GNCGGG (SEQ ID NO: 57), CGGSCG (SEQ ID NO: 58), GSTSCG (SEQ ID NO: 59), DGGCSG (SEQ ID NO: 60), ATSCGG (SEQ ID NO: 61), ASCGYG (SEQ ID NO: 62), DGACGG (SEQ ID NO: 63), GGSGSGSGG (SEQ ID NO: 26), GGGSGGGSGGGTGGGSGGGR-RADAA (SEQ ID NO: 27), SRAWRHPQFGG (SEQ ID NO: 28), RAFIASRRIRRP (SEQ ID NO: 29), RLLLR-RLRR (SEQ ID NO: 30), RIIIRRIRR (SEQ ID NO: 41), AAS, NDN, PSNTNHNSNSN (SEQ ID NO: 31), SHRAT-PNTSPH (SEQ ID NO: 32) and combinations thereof.

In preferred embodiments, the probe attached to the solid substrate is tagged for attachment to the solid substrate. Preferably, the tag includes one or more of His-tag, biotin, Flag-epitope, c-myc epitope, HA-tag, glutathione-S-transferase (GST), maltose binding protein (MBP), a chitin binding domain (CBD), Thioredoxin, β-Galactosidase, VSV-Glycoprotein, calmodulin binding protein, a polystyrene (PS) hydrophobic tag, and a metal affinity tag.

In some preferred embodiments, the solid substrate includes a second fluorophore, optionally attached to a protein that does not bind FFAu.

In preferred embodiments, the probe attached to the solid substrate includes a tag and the solid substrate has a receptor for the tag. Preferably, the tag is a poly-histidine tag and the solid substrate includes an immobilized metal chelate.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
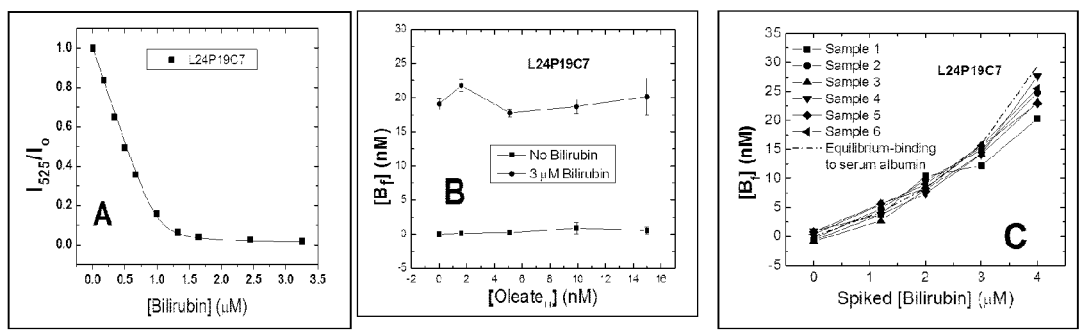
FIG. 1A shows $I_{525}/I_0$ versus bilirubin concentration for probe L24P19C7 (SEQ ID NO: 36).
FIG. 1B shows measured free bilirubin concentrations $[B_f]$ versus oleate concentration for probe L24P19C7 (SEQ ID NO: 36) in the presence and absence of bilirubin (3 μM).
FIG. 1C shows free bilirubin concentrations $[B_f]$ versus increasing concentration of added bilirubin for probe L24P19C7 (SEQ ID NO: 36).

While the described embodiment represents the preferred embodiment of the present invention, it is to be understood that those skilled in the art can modify the process without departing from the spirit of the invention.

For purposes of the present disclosure, "analytes" are molecules whose molecular weight is approximately 2000 Da or less and unbound analytes are these molecules in aqueous solution. These include metabolites and physiologically important molecules that occur naturally in the course of human or animal physiology or pathophysiology, and drug molecules and their metabolic products and nutrient molecules and their metabolic products. Depending upon their solubility, a fraction of each analyte is present as monomers in aqueous solution (either charged or neutral). This fraction is referred to as the "free or unbound analyte" fraction and includes unbound metabolites (METu).

For purposes of the present disclosure bilirubin is unconjugated bilirubin IXα [McDonagh A F, Vreman H J, Wong R J and Stevenson D K. Photoisomers: obfuscating factors in clinical peroxidase measurements of unbound bilirubin? *Pediatrics* 123: 67-76, 2009]. Unbound bilirubin is the aqueous monomer of the unconjugated bilirubin IXα, as distinct from bilirubin that in blood plasma is generally found bound to albumin.

For the purposes of the present disclosure, the term "lipid" is taken to have its usual and customary meaning and defines a chemical compound which is most soluble in an organic solvent but has some level of solubility in the aqueous phase (the fraction that is unbound). Accordingly, a "lipid-binding protein" includes any protein capable of binding a lipid as lipid is defined herein.

Levels of unbound molecules, such as for example bilirubin, lipids, including fatty acids, hormones and metabolic products, can provide information diagnostic of health and disease when measured in appropriate human or animal fluids. It is increasingly apparent that determination of the unbound (a.k.a 'aqueous phase' or 'free') concentration of such molecules provides critical information about physiologic homeostasis. Many metabolites are hydrophobic molecules with low aqueous solubility and unbound concentrations that are much lower than their "total" concentration, where the bulk of the "total" may be bound to proteins or cells. In biological fluids the concentration of the unbound molecules is often regulated to maintain a relatively constant unbound concentration under normal physiologic conditions. This regulation occurs through the interaction of the molecules with a carrier protein such as for example, albumin. Thus most of the molecules are generally bound to albumin, or other carriers. However a small fraction of the molecules may dissociate (and rebind) from the albumin into the aqueous phase and these are the unbound molecules.

For the purposes of the present disclosure "bilirubin probes" are iLBPs that are fluorescently labeled at one or more cysteine or lysine residues and that undergo a change in a fluorescence index upon binding bilirubin. A bilirubin probe may also be an iLBP fluorescently labeled at a cysteine residue with one fluorophore and at a different, preferably lysine, residue with a different fluorophore so that if the fluorescence of only one of the fluorophores changes upon binding bilirubin the ratio of fluorescence indices at 2 wavelengths will be different. A bilirubin probe may also comprise an iLBP fluorescently labeled at a cysteine or lysine residue with additional fluorescence provided by a second fluorophore that is not attached to the probe protein. In this case, if the fluorescence of only one of the fluorophores changes upon binding bilirubin the ratio of fluorescence indices at 2 wavelengths will be different. The second fluorophore may be a fluorescent molecule free in aqueous solution or may be attached to a larger molecule, such as an iLBP, that is not responsive and/or does not bind to bilirubin or the second fluorophore may be attached to a surface or the non-responsive molecule attached to the second fluorophore, may be attached to the surface. Such probes may be used to determine specifically the aqueous concentration of unbound bilirubin, which is otherwise difficult because of its poor solubility properties in aqueous solutions and because of the presence of other metabolites especially free fatty acids. A change in the ratio of the fluorescence response is especially important for the accurate determination of the intracellular concentrations of unbound bilirubin and is important for improving the accuracy and precision of the determination of the extracellular concentrations of unbound bilirubin.

Unfortunately, despite the availability of protein structures and co-complex structures with ligands of interest, existing state of the art of molecular theory is not sufficient to design probes with any desired metabolite specificity and sensitivity de novo. Thus, extensive experimentation is typically required to find mutant protein probes that not only bind with the desired specificity, but also produce the required change in signal indicative of ligand binding. Screening even a single protein for its binding affinity for bilirubin and specificity to a range of additional analytes requires extensive time for protein purification, the development of methods to measure binding of different analytes and the measurement of each analyte's binding isotherms. [Systematic high throughput screening of mutant proteins is not possible because in general mutant proteins without a fluorescence label do not elicit a measurable signal upon analyte binding.] Once the protein-analyte interaction is characterized additional experimentation is required for the fluorophore reaction chemistry and the probe fluorescence response characterization. Moreover, in general the analyte-protein binding properties are different than those for the analyte-probe interaction. Thus the probe developed using a protein, found after extensive experimentation to have the desired binding specificity for bilirubin, may not generate a significant fluorescence change upon bilirubin binding. Instead, what is needed are methods to rapidly generate and screen thousands of resulting mutant probes.

U.S. Pat. No. 7,601,510 and U.S. publication 2010/0298162 which are incorporated herein by reference, and [Huber A H, Kampf J P, Kwan T, Zhu B and Kleinfeld A M. Fatty acid-specific fluorescent probes and their use in resolving mixtures of different unbound free fatty acids in equilibrium with albumin. *Biochemistry* 45: 14263-14274, 2006] describe methods for high throughput generation of probes that allow for the development of probes with high specificity for the determination of unbound analytes. Both U.S. Pat. No. 7,601,510 and U.S. publication 2010/0298162 describe the development of bilirubin specific probes. The current invention relates to critical improvements in the bilirubin technology described in U.S. Pat. No. 7,601,510 and U.S. publication 2010/0298162 that improve the accuracy and precision for the determination of unbound bilirubin levels and that allow the technology to be used in different instrumentation formats. [Importantly, these previous bilirubin probes described in U.S. Pat. No. 7,601,510 and U.S. publication 2010/0298162 were not ratio probes. The current invention relates to the novel method of generating ratio probes by a using a second fluorophore that is not attached to the bilirubin sensitive probe to which the first fluorophore is attached. The current invention also relates to the surprising quenching of long wavelength probes by bilirubin. In addition the invention relates to methods of attaching bilirubin and FFAu probes to solid surfaces and using such compositions for measuring unbound bilirubin and FFAu in microfluidics devices and disposable sample cartridges.

Bilirubin probes are used to determine unbound bilirubin levels in blood samples and fatty acids are the most abundant metabolite in blood that have properties similar to bilirubin. Fatty acids compete with bilirubin for binding to albumin and have unbound concentrations that are similar to bilirubin. Bilirubin probes are developed starting with iLBP mutants that generally have high affinity for fatty acids. Thus the first step in discovering bilirubin probes from iLBP mutein probes is the screening of more than 300,000 such probes with up to 11 of the most abundant fatty acids to identify probes that do not significantly respond to fatty acids. More than 10,000 such fatty acid non-responders ("non-responder library") have been identified by $\Delta R/\Delta R_{ADIFAB2}$ (U.S. Pat. No. 7,601,510)<0.1. This quantitative benchmark indicates that the affinity of these probes for fatty acids are in general at least 10 fold smaller than for ADIFAB2 reference probe. Screening these non-responder probes with bilirubin identifies potential bilirubin probes and/or templates that are used for the generation of new mutein probe libraries by further mutagenesis of the newly identified template protein. This new library is screened for response to fatty acids and bilirubin and the probes identified as most responsive to bilirubin and least responsive to fatty acids are either identified as bilirubin probes or may be used for further rounds of mutagenesis and screening.

Bilirubin probes identified by these methods to have useful properties, including a significant response to bilirubin and zero to low response to fatty acids are further characterized. A probe that does not respond significantly to FFA means that binding to FFA is 10 times less than binding to bilirubin. Preferably, binding to FFA is 100 times less than binding to bilirubin. This includes calibration to determine probe bilirubin binding affinity and fluorescence characteristics, as well as monitoring unbound bilirubin levels in aqueous solutions containing bilirubin and human serum albumin in order to identify potential competition with fatty acids. Non-responsive probes might be generated in which fatty acids bind to the probe but do not generate a change in fluorescence. In this case fatty acids in blood samples might compete with bilirubin for binding to the probe and thereby result in an inaccurate determination of the unbound bilirubin levels. Competition with fatty acids is evaluated by determining whether the fluorescence response of a bilirubin probe plus bilirubin is altered by addition of fatty acids.

Bilirubin probes found by the above methods to yield accurate bilirubin concentrations in solutions with bilirubin and albumin and which do not exhibit detectable fatty acid competition are selected for further testing in human blood samples. Blood plasma samples from individual donors as well as pooled samples from commercial sources are used to determine whether the bilirubin probes provide accurate plasma unbound bilirubin concentrations in samples that have essentially unknown levels of analytes commonly present in human blood samples. This is accomplished by determining the albumin concentration in each sample and titrating the blood samples with bilirubin to obtain well-defined bilirubin:albumin ratios. The concentration of unbound bilirubin is then measured with the probe and the results compared with a) the unbound bilirubin concentrations measured in aqueous bilirubin-albumin solutions having the same bilirubin:albumin ratios and b) with unbound bilirubin concentrations determined using the peroxidase assay [Jacobsen J and Wennberg R P. Determination of unbound bilirubin in the serum of newborns. *Clin Chem* 20: 783, 1974]. Equivalence of the probe determined plasma unbound bilirubin concentrations with those determined in bilirubin-albumin solutions and with the peroxidase assay confirms that blood components other than unbound bilirubin have no detectable effect on the probe performance.

An important aspect of U.S. Pat. No. 7,601,510 and U.S. publication 2010/0298162 is that they allow the previously necessary and very time consuming step of characterization of bilirubin binding to the protein to be omitted; only the probe itself is characterized. This is important not only for the avoidance of the protein characterization step but also because the properties of the probe are often not predictable from the ligand-protein binding characteristics. For example, different proteins can have very similar binding affinities but the fluorescence response of their derivative probes can be quite different.

Bilirubin probes described previously were labeled only with acrylodan, primarily at lysine 27 of SEQ 3: (U.S. Pat. No. 7,601,510). Additional bilirubin probes were labeled with two different fluorophores, acrylodan at lysine 27 of SEQ 3: and Texas red maleimide at the cysteine of an N terminal MGCFD adduct in two versions one without and the other with the KR14 ("KR14" is an abbreviation that refers to the mutation of the following 14 surface lysines to arginine in SEQ 3: 7R 16R 20R 29R 37R 46R 50R 88R 92R 94R 100R 125R) substitution that reduces multiple acrylodan labeling (U.S. publication 2010/0298162). These probes have good affinities and responses to bilirubin and were not significantly affected by non-bilirubin metabolites in human blood samples. However the acrylodan-only probes may be adversely affected by bilirubin-mediated excitation inner filter effect in samples with high bilirubin concentrations, a condition in severe neonatal hyperbilirubinemia [Bhutani V K and Johnson L. The Jaundiced Newborn in the Emergency Department: Prevention of Kernicterus. Clin Ped Emerg Med 9:149-159, 2008], and by the presence of hemoglobin in the blood sample. Double labeled probes with acrylodan plus a longer wavelength fluorophore, such as Texas Red, can have severely reduced acrylodan fluorescence intensities due to energy transfer between acrylodan and the secondary fluorophore.

To overcome these deficiencies and to extend the spectrum of instruments on which the bilirubin probes can be used, the present invention describes new probes and new forms of the assay for determining unbound bilirubin levels. New mutein libraries were identified in which the fluorophore quenched by bilirubin labels either a single cysteine or lysine side chain and the position of this side chain is found to be important for optimizing the fluorescence change upon bilirubin binding. Also identified are bilirubin probes in which the fluorophore quenched by bilirubin labels one or more cysteine or lysine side chains but where the position of one of the side chains is found to be important for optimizing the fluorescence change upon bilirubin binding. Also discovered are bilirubin quenchable fluorophores that absorb and emit at long wave lengths where bilirubin quenching by Förster type energy transfer should not occur. Bilirubin binding produces virtually complete quenching of acrylodan and other fluorophores whose emission occurs in the range of approximately 380 nm to 550 nm, which is expected because of the high degree of Förster type energy transfer due to the large overlap of acrylodan and the emissions of other fluorophores with bilirubin absorbance. Entirely unexpected was the discovery of fluorescence quenching by bilirubin of very long wavelength fluorophores including those extending into the infrared (TABLES 5 and 7). Because of their long wavelength absorbance and fluorescence such fluorophores are unaffected by bilirubin or hemoglobin absorbance or that of virtually any other chromophore potentially present in blood samples.

Additional embodiments of the invention described here are methods to generate bilirubin ratio probes that are generated with a single fluorophore on the protein and with a second different fluorophore either (a) free in solution, (b) attached to a larger molecule, such as polymer, that is not responsive and/or does not bind to bilirubin, (c) embedded in resin or polymer, or (d) attached, directly or indirectly, to a surface. Such a probe responds to bilirubin binding to the protein portion of the probe with a change in the ratio of a fluorescence index measured at two different wavelengths. This also allows probes that do not reveal a ratio fluorescence index change in response to bilirubin binding to be converted readily into a ratio probe by using a second but unattached fluorophore that reveals no significant response to bilirubin. This type of ratio probe, one that uses an independent second fluorophore, eliminates the problem of energy transfer quenching between fluorophores that is typically observed when both fluorophores are located on the same macromolecule such as a protein. This quenching greatly reduces the signal intensity and thereby diminishes the accuracy and precision of the measurement of the unbound bilirubin concentration. This avoidance of energy transfer is accomplished by not attaching both fluorophores to the same probe molecule. Otherwise the avoidance of energy transfer would need to be accomplished by spatially restricting the fluorophores when the second fluorophore is attached to the same small protein.

Also described are bilirubin probes that can attached to solid substrates such as polystyrene or latex beads and which beads can be immobilized on a surface for use in disposable microfluidics devices. Additionally a second fluorophore can be attached or embedded within the beads thereby separating the two fluorophores so as to eliminate energy transfer and thereby obtain a ratio response to bilirubin binding. Alternatively the second fluorophore can be attached to an iLBP or any other polymer that is not responsive to and/or does not bind bilirubin and which iLBP or other polymer is attached to the solid substrate so that the two fluorophores remain sufficiently separated so that energy transfer is not significant.

Also described are analytical/mathematical methods for calibrating and using the bilirubin probes. Bilirubin probes are calibrated to determine their binding affinity for bilirubin (dissociation constant $K_d$) under conditions, such as temperature, pH and solution composition, that correspond to samples in which it is desired to know the unbound bilirubin concentration. Binding isotherms are performed in aqueous buffer by measuring the change in fluorescence of the bilirubin probes in response to increasing bilirubin concentrations ("titration data"). The set of fluorescence responses at each bilirubin concentration are fitted with an appropriate equation ("calibration equation") that correctly describes the fluorescence response as a function of the bilirubin concentration, the probe concentration, specific spectroscopic characteristics, and the $K_d$.

In some embodiments the bilirubin absorbance overlaps with the excitation wavelength of the bilirubin probe's fluorophore and the calibration is performed in a cuvette where the path length d is sufficiently large that inner filter absorbance is significant. In this case the emission intensities of the fluorophore must be corrected for inner filter absorbance due to bilirubin absorbance at the excitation wavelength and possibly at the emission wavelength prior to fitting the calibration equation to the bilirubin probe's titration data. The equation for the corrected emission intensities ($I_{\lambda em}^{Corr}$) is:

$$I_{\lambda em}^{Corr} = I_{\lambda em} 10^{B_T \epsilon(\lambda ex)\frac{d}{2}} \quad (1)$$

where $I_{\lambda em}$ is the measured fluorescence emission intensity at the wavelength $\lambda_{em}$, $B_T$ is the total bilirubin concentration, $\epsilon(\lambda_{ex})$ is the bilirubin extinction coefficient at the excitation or emission wavelength ($\lambda_{ex}$) and d is the cuvette path length. As equation (1) indicates the inner filter correction requires knowledge of the total bilirubin concentration ($B_T$), which must also be measured in order to determine [$B_f$].

The inner filter excitation correction is important for single fluorophore, non-ratio, bilirubin probes for which the calibration equation is:

$$\frac{I_{\lambda em}}{I_o} = 1 - \frac{(K_d + B_t + P_T) - \sqrt{(K_d + B_t + P_T)^2 - 4B_T P_T}}{2P_T} \quad (2)$$

where $I_{\lambda em}$ is the fluorescence intensity of the probe in the sample with blank (sample without bilirubin probe) subtracted, and if inner filter absorbance is significant $I_{\lambda em}^{Corr}$ from equation (1) must be substituted for $I_{\lambda em}$ in equation (2), $I_o$ is the intensity of the probe in the absence of bilirubin, $P_T$ is the total bilirubin probe concentration and $B_T$ is the total bilirubin concentration.

The inner filter excitation correction is important for single fluorophore probes but does not affect the response of ratio bilirubin probes, which respond to bilirubin by a change in the ratio of fluorescence emissions (I$\lambda$1/I$\lambda$2) at two wavelengths $\lambda$1 and $\lambda$2. The ratio, or R value, is equal to I$\lambda$1/I$\lambda$2. Bilirubin titration of the ratio probe to determine the Kd, is well described by the following calibration equation (3):

$$R = -\frac{\sqrt{(P_T^2 + (2K_d - 2B_T)P_T + K_d^2 + 2B_T K_d + B_T^2)}\,(rR_o^2 - R_o) +}{2(B_T r^2 R_o^2 - (P_T + K_d + B_T)rR_o + P_T)} \quad (3)$$

$$\phantom{R = -}\frac{(P_T + K_d - B_T)rR_o^2 + (-P_T + K_d + B_T)R_o}{2(B_T r^2 R_o^2 - (P_T + K_d + B_T)rR_o + P_T)}$$

where R is the measured fluorescence ratio (($I_{\lambda 1}/I_{\lambda 2}$), $R_o$ is the ratio in the absence of bilirubin, r is the ($I_{\lambda 2}/I_{\lambda 1}$) ratio of the probe in the absence of the second fluorophore, $B_T$, $P_T$, and $K_d$ are the same as in equation (2).

Free bilirubin concentrations ([$B_f$]) are determined in samples in which [$B_f$] is buffered by the HSA binding equilibrium and is therefore not perturbed by the presence of the bilirubin probe. The following equations are for single (4) fluorophore and ratio (5) probes respectively:

$$[B_f] = K_d\left(\frac{I_o}{I_{\lambda em}} - 1\right). \quad (4)$$

and $$[B_f] = K_d\left(\frac{(R - R_o)}{(RrR_o - R)}\right) \quad (5)$$

Preferred embodiments of the present invention relate to the development of fluorescent protein molecules that can be used to determine the concentration of unbound analytes. More particularly, the invention relates to 1) Identification of bilirubin probes generated by the methods of U.S. Pat. No. 7,601,510 and U.S. publication 2010/0298162 which are incorporated herein by reference and modifications of these methods are also described, 2) the use of such probes for clinical medicine and basic science, 3) examples of these probes for the determination of the unbound bilirubin concentration in different fluids.

Bilirubin probes are iLBP proteins that have been 'labeled' through the covalent addition of one or more fluorescent molecule(s) (fluorophore(s)) that exhibit a change in a fluorescent index upon binding bilirubin. In preferred embodiments, the probe contains either a single cysteine or a single accessible lysine to which a fluorophore is covalently attached. In other preferred embodiments, the probe includes one fluorophore attached to a cysteine and a second fluorophore attached to a different site, preferably a lysine site, on the protein which binds bilirubin. In other preferred embodiments the probe includes one fluorophore attached to a cysteine and a second fluorophore attached to a different site, preferably a terminal amino group, on the protein which binds bilirubin.

In some embodiments, two different fluorophores are used, preferably attached to a cysteine and a lysine or to a cysteine and an N-terminus amino group. One of the two fluorophores is responsive to bilirubin binding, that is, demonstrating a change in a fluorescence index upon binding of bilirubin to the probe. The second fluorophore may be sensitive to bilirubin binding but it is not necessary for the second fluorophore to be responsive to binding of bilirubin. The second fluorophore provides a reference point so that a difference in ratio of fluorescence at two different wavelengths is observed upon bilirubin binding. The second fluorophore may not react to the bilirubin binding or may react in a different manner from the first fluorophore. Preferably, the second fluorophore has an emission point at a different wavelength relative to the first fluorophore. Examples of chemical dyes which may be used as a second fluorophore according to the invention include but are not limited to Alexa Fluor dyes, Bodipy dyes, fluorescein derivatives, rhodamine derivatives and Texas red. In a preferred embodiment, the second fluorophore is Texas red.

In some embodiments, two different fluorophores are used in which one fluorophore is attached to a cysteine or a lysine or the N-terminus amino group and this fluorophore is responsive to bilirubin binding, that is, demonstrating a change in a fluorescence index upon binding of bilirubin to the fluorescently labeled iLBP mutein, The second fluorophore is not chemically linked to the iLBP mutein and is not sensitive to bilirubin binding to the iLBP mutein. The second fluorophore provides a reference point so that a difference in ratio of fluorescence at two different wavelengths is observed upon bilirubin binding. In one embodiment the second fluorophore is soluble and is mixed together with the fluorescently labeled iLBP mutein at a defined stoichiometry of fluorescently labeled iLBP mutein to the second soluble fluorophore. This mixture may be maintained in solution or dried or lyophilized and then reconstituted when needed. This mixture constitutes a bilirubin probe that responds by a difference in ratio of fluorescence at two different wavelengths. This configuration of a bilirubin probe with a soluble second fluorophore is advantageous because the absorbance spectrum of a second longer wavelength fluorophore may overlap with the emission of the first shorter wavelength fluorophore. This can significantly quench the fluorescence of the first fluorophore, and thereby diminish the signal quality of the probe response, when both are chemically attached to the same iLBP protein. An additional advantage is that the stoichiometry of the first to the second fluorophore is more easily regulated and simpler to prepare than for the stoichiometry dependent on the two separate chemical reactions of the first and second fluorophore with the iLBP mutein. Preferably, the second fluorophore has an emission point at a longer wavelength relative to the first fluorophore. Examples of chemical dyes which may be used as the first fluorophore include but are not limited to acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino-7-nitrobenz-2-oxa-1,3-diazole (IANBDA). Examples of chemical dyes which may be used as a second fluorophore according to the invention include but are not limited to Alexa Fluor dyes, Bodipy dyes, fluorescein derivatives, rhodamine derivatives and Texas red. In a preferred embodiment, the first fluorophore is acrylodan labeled either at cysteine or lysine and the second fluorophore is Rhodamine B.

Alternatively the protein may be "tagged" so that it binds to a solid support with high affinity. This includes but is not limited to tagging with biotin, Flag-epitope or c-myc epitope or HA-tag, glutathione-S-transferase (GST), maltose binding protein (MBP), a chitin binding domain (CBD), Thioredoxin, β-Galactosidase, VSV-Glycoprotein, calmodulin binding protein, a polystyrene (PS) hydrophobic tag or a metal affinity tag such as a 6×His tag. The specific association of the affinity tag with the solid support material facilitates unbound bilirubin measurements in flat surface configurations including but not limited to multi-well plates and microfluidics devices. By virtue of their attachment to solid supports the probes can be concentrated in a restricted, effectively two dimensional region. This enables measurements of unbound bilirubin within thin layers of sample solutions allowed to flow across the probes, which are confined to the effectively two dimension region. This effectively allows for front surface fluorescence measurements which reduces absorbance due to bilirubin and hemoglobin and facilitates measurements in whole blood. This configuration also allows for the possibility of repeated, samples alternating with a wash bolus, or continuous measurements of unbound bilirubin by flowing sample continuously across the two dimensionally confined probes. The affinity tag(s) may be fused at either the NH2- or COOH— termini or at both termini simultaneously as shown for example in Table 8. In a preferred embodiment, a 6× Histidine tag was fused to either the FABP $NH_2$— or COOH— termini or at both termini simultaneously without significantly changing the protein's bilirubin binding properties. In preferred embodiments the fusion peptide is composed of two separated Histidine regions at the COOH terminus of the probe. Also in a preferred embodiment the probes are immobilized on a solid support including but not limited to Ni-polystyrene beads with or without iron cores. The iron cores facilitate magnetically concentrating the probe-beads in the effectively two dimension regions of multiwell plates, microfluidic groves or other devices compatible with fluorescence measurements from effectively two dimensional regions.

In some embodiments the bilirubin probe immobilized on a solid support protein is a combination of two proteins labeled with different fluorophores that excite at the same wavelength but emit at two different wavelengths. One of the two proteins is responsive to bilirubin binding that is, it demonstrates a change in a fluorescence index upon binding of bilirubin to the protein. The second protein labeled with a different fluorophore may be sensitive to bilirubin binding but it is not necessary for the second protein to be responsive to binding of bilirubin. The second protein's fluorophore provides a reference point so that a difference in ratio of fluorescence at two different wavelengths is observed upon bilirubin binding. In a preferred embodiment the first, bilirubin sensitive, protein is labeled with 700DX and the second bilirubin insensitive protein is labeled with Texas Red, Bodipy Dyes or Alexa Fluor Dyes.

Using the Probes

In preferred embodiments of the invention, the sample used for the determination of unbound bilirubin is a fluid sample derived from a human, an animal or a plant. Preferably, the fluid is whole blood, blood plasma, blood serum, urine, CSF, saliva, gastric juices, interstitial fluid or lymph. In other embodiments determination of unbound bilirubin is performed within the cytoplasm of a cell by microinjecting or otherwise transfecting the probe into the cell or is performed in the extracellular media of the cells.

A normal range for unbound bilirubin is determined from a healthy population and deviations from this normal range may indicate disease.

Unbound bilirubin probes are calibrated and used for measurements of $[B_f]$ using equations 1-5 and as described in [Huber A H, Zhu B, Kwan T, Kampf J P, Hegyi T and Kleinfeld A M. Fluorescence Sensor for the Quantification of Unbound Bilirubin Concentrations. *Clin Chem* 58: 869-876, 2012].

Unbound bilirubin probes are used for measurements of $[B_f]$ in patients at risk for bilirubin mediated toxicity, such as 60% of newborns who have insufficient liver function to eliminate excess bilirubin [Maisels M J and McDonagh A F. Phototherapy for neonatal jaundice. *N Engl J Med* 358: 920-928, 2008].

Unbound bilirubin probes are used for measurements of $[B_f]$ in patients receiving intravenous infusions of oil emulsions as well as in patients with diseases that can increase $[B_f]$ by decreasing the binding affinity of bilirubin for albumin, such as sepsis, which is common in premature newborns and increases FFA levels [Nogueira A C, Kawabata V, Biselli P, Lins M H, Valeri C, Seckler M, Hoshino W, Junior L G, Bernik M M, de Andrade Machado J B, Martinez M B, Lotufo P A, Caldini E G, Martins E, Curi R and Soriano F G. Changes in plasma free fatty acid levels in septic patients are associated with cardiac damage and reduction in heart rate variability. *Shock* 29: 342-348, 2008].

Unbound bilirubin probes are used for measurements of [$B_f$] in patients receiving phototherapy, transfusion or other therapies designed to reduce bilirubin toxicity.

Because unbound bilirubin not total bilirubin is toxic, unbound bilirubin not total bilirubin should be monitored during phototherapy to ensure that unbound bilirubin decreases significantly. Although total bilirubin has been shown to decrease in response to phototherapy, in the presence of bilirubin displacing molecules such as FFA, total bilirubin and unbound bilirubin can be almost completely decoupled. Under these conditions virtually complete destruction of total bilirubin might be required to lower unbound bilirubin levels to those considered non-toxic. Thus total bilirubin levels would be required that are much lower than currently achieved even for aggressive therapy. Moreover, the peroxidase assay cannot be used to monitor unbound bilirubin during phototherapy because this test does not distinguish between photoproducts (and conjugated bilirubin) and the "native" unconjugated IX-α isomer. In contrast unbound bilirubin measured with the probes described in this application are specific for the native unconjugated IX-α.

The only method currently used for determining unbound bilirubin is based on horseradish peroxidase oxidation of bilirubin [Jacobsen J and Wennberg R P. Determination of unbound bilirubin in the serum of newborns. *Clin Chem* 20: 783, 1974]. Implementation of the peroxidase assay is available using an FDA approved instrument (Arrows Ltd, Osaka, Japan). Adoption of this method for the general screening of jaundiced newborns has been limited because of issues with the Arrows method that complicate accurate unbound bilirubin determinations [Ahlfors C E. Measurement of plasma unbound unconjugated bilirubin. *Anal Biochem* 279: 130-135, 2000; Ahlfors C E, Vreman H J, Wong R J, Bender G J, Oh W, Morris B H and Stevenson D K. Effects of sample dilution, peroxidase concentration, and chloride ion on the measurement of unbound bilirubin in premature newborns. *Clin Biochem* 40: 261-267, 2007]. Most importantly multiple, relatively large sample volume, measurements are required to determine the equilibrium unbound bilirubin concentration and corrections are needed for interferents and sample dilutions, using the Arrows method.

Embodiments of the invention provide a new method for measuring unbound bilirubin that overcomes the shortcomings of the peroxidase—Arrows method. This new method uses fluorescently labeled fatty acid binding proteins (unbound bilirubin probes) that allow direct monitoring of the equilibrium unbound bilirubin concentration. The probes are specific for unconjugated bilirubin and bind bilirubin with high affinity. Moreover, unbound bilirubin probes are highly specific for unbound bilirubin and do not respond or bind significantly to free fatty acids (FFA), other metabolites and drugs present in blood. The unbound bilirubin probes are used to determine unbound bilirubin levels in jaundiced patients including neonates to diagnose potential bilirubin neurotoxicity and thereby accurately direct treatment to prevent the consequences of such toxicity.

EXAMPLES

The following definitions are with reference to SEQ ID NO: 3.

"KR6" refers to the mutation of the following 6 surface lysines to arginine: 7R 20R 46R 100R 125R 130R.

"KR14" refers to the mutation of the following 14 surface lysines to arginine: 7R 16R 20R 29R 37R 46R 50R 88R 92R 94R 100R 125R 129R 130R.

"MGI" refers to the mutation of the wild-type NH2-terminus sequence of MAFD (SEQ ID NO: 37) to MGIFD (SEQ ID NO: 38). In each case, the N-terminal methionine is removed by the cell to generate the mature protein.

"MGCFD (SEQ ID NO: 39)" refers to the mutation of the wild-type NH2-terminus sequence of MAFD (SEQ ID NO: 37) to MGCFD (SEQ ID NO: 39). In each case, the N-terminal methionine is removed by the cell to generate the mature protein.

"MGGSATGIFD (SEQ ID NO: 40)" refers to the mutation of the wild-type NH2-terminus sequence of MAFD (SEQ ID NO: 37) to MGGSATGIFD (SEQ ID NO: 40). In each case, the N-terminal methionine is removed by the cell to generate the mature protein.

Example 1

L24P19C7 (SEQ ID NO: 36)

Bilirubin probes are derived from a rat intestinal fatty acid binding protein (rI-FABP) as described previously for unbound FFA (FFAu) probes in U.S. Pat. No. 7,601,510, U.S. publication 2010/0298162 and [Huber A H, Zhu B, Kwan T, Kampf J P, Hegyi T and Kleinfeld A M. Fluorescence Sensor for the Quantification of Unbound Bilirubin Concentrations. *Clin Chem* 58: 869-876, 2012; Huber A H, Kampf J P, Kwan T, Zhu B and Kleinfeld A M. Fatty acid-specific fluorescent probes and their use in resolving mixtures of different unbound free fatty acids in equilibrium with albumin. *Biochemistry* 45: 14263-14274, 2006]. Combinatorial mutagenesis is used first to generate and screen mutant probes for responses to FFAu. Among these probes about 10% do not respond significantly to FFAu and are screened further for their response to unconjugated bilirubin. Hits from this screen are selected for additional mutagenesis to increase the affinity and selectivity for unbound bilirubin. An example from the results of these methods is the acrylodan labeled L24P19C7 (SEQ ID NO: 36) which respect to SEQ 3 has the mutations: 14R 18L 38V 60R 73F 106C 115R and 117D (Table 5). The acrylodan reaction, at pH 9.3, primarily labels L24P19C7 (SEQ ID NO: 36) at the K27 side chain. L24P19C7 (SEQ ID NO: 36) was calibrated at 22° C. with aqueous bilirubin and by fitting with equation (5) yielded a $K_d$ of 22 nM and virtually complete quenching at bilirubin concentrations approaching saturation (the remaining fractional intensity ($Q_s$)=0.0042) (FIG. 1A). L24P19C7 (SEQ ID NO: 36) is not responsive to free fatty acids (FFA). Titrating L24P19C7 (SEQ ID NO: 36) with unbound oleate either in the presence or absence of bilirubin produces no change in its fluorescence or equivalently the unbound bilirubin concentration (FIG. 1B). The FFA concentrations in FIG. 1B, of unbound oleate (the most abundant FFA in human blood plasma) are more than 10-fold higher than the concentration in human plasma. In addition to its lack of response to FFA, L24P19C7 (SEQ ID NO: 36) is also not responsive to other metabolites present in human plasma. Measurements of unbound bilirubin in 6 different adult blood plasma samples spiked with bilirubin demonstrate that in the absence of bilirubin the unbound concentration is less than 1 nM and that the increase in unbound bilirubin follows the behavior predicted for the equilibrium between bilirubin and serum albumin.

Example 2

L24P19C7 (SEQ ID NO: 36)-Xc

Figure 2:
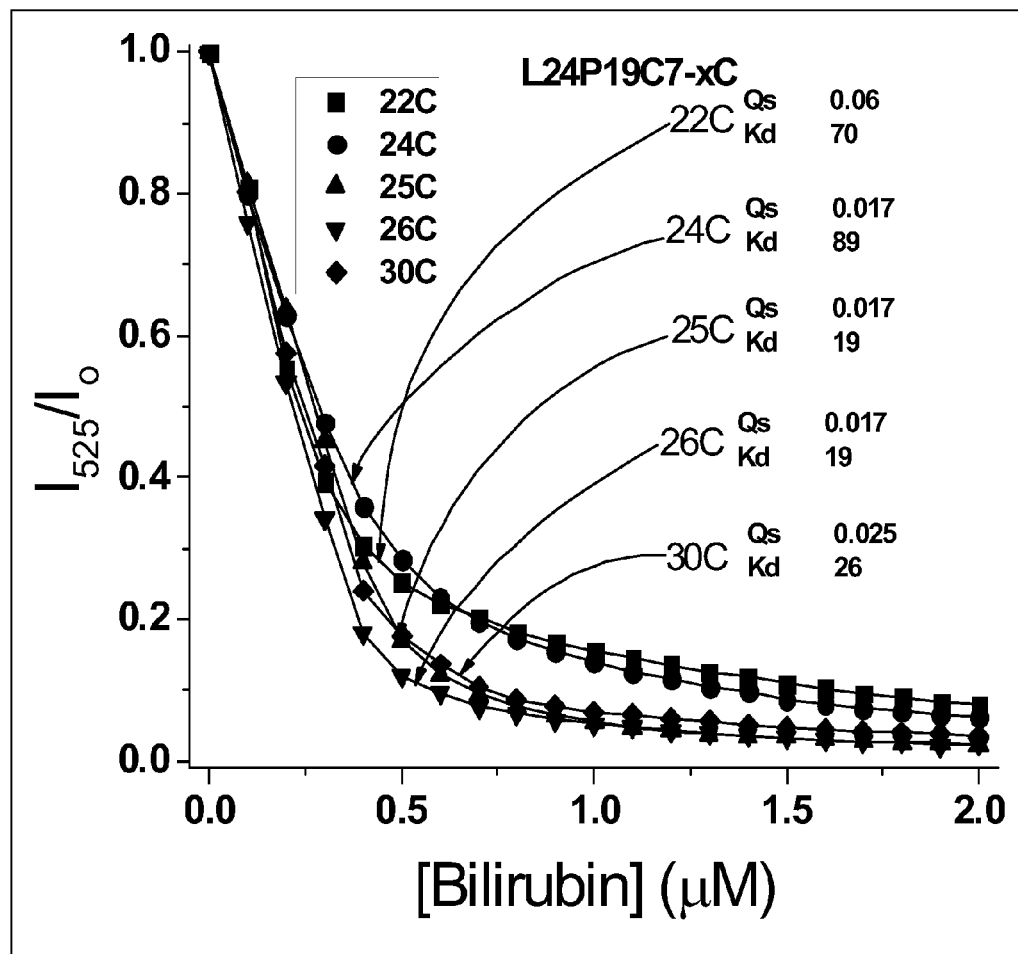
FIG. 2 shows $I_{525}/I_0$ versus bilirubin concentration for probe L24P19C7 (SEQ ID NO: 36)-Xc, where Xc denotes different single cysteine positions labeled with acrylodan.

Mutants of L24P19C7 (SEQ ID NO: 36) were synthesized in which a single cysteine was substituted at side chain positions between 22 and 30 to generate probes with stable, essentially unique, sites of acrylodan labels and to optimize the interaction of bilirubin with the probe (FIG. 2). The results demonstrate that $K_d$ for bilirubin binding ranges from 19 to 89 nM and the degree of quenching of acrylodan fluorescence ($Q_s$) ranges from about 1.7 to 6%. The optimal probe performance was obtained with cysteine at positions 25 or 26. This demonstrates that tuning of the probe performance requires minimal experimentation after its basic structure has been identified.

Example 3

BL22P1B11 (SEQ ID NO: 35)

TABLE 1

$K_d$s for binding BL22P1B11 (SEQ ID NO: 35)

| | $K_d$ (nM) |
|---|---|
| Bilirubin | 16 |
| Docosahexaenoate 22:6 (n-3) | 4300 |
| Arachidonate 20:4 (n-6) | 28600 |
| Linolenate 18:3 (n-3) | 3460 |
| Linoleate 18:2 (n-6) | 3120 |
| Oleate 18:1 (n-9) | 2510 |
| Stearate 18:0 | 75500 |
| Palmitoleate 16:1 (n-7) | 3140 |
| Palmitate 16:0 | 3200 |
| Myristate 14:0 | 23400 |

Figure 3:
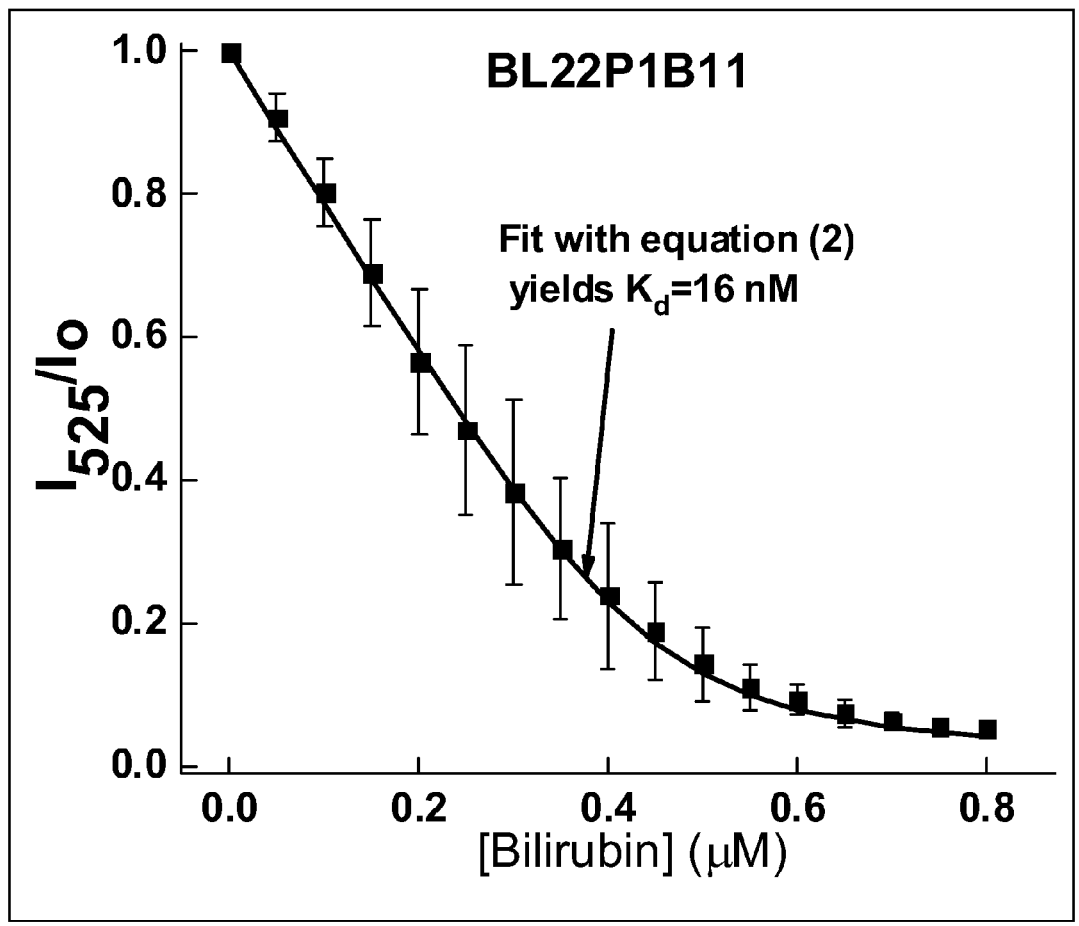
FIG. 3 shows results in spiked adult serum. $I_{525}/I_0$ versus increasing concentration of added bilirubin for probe BL22P1B11 (SEQ ID NO: 35) is shown.

BL22P1B11 (SEQ ID NO: 35) is a bilirubin probe which is labeled with only a single fluorophore, in this case acrylodan at position 25 by virtue of the removal of 14 surface lysines (KR14), the lysine at 27 and, relative to L24P19C, the cysteine at 106. Thus BL22P1B11 (SEQ ID NO: 35) has the structure: MGI-KR14-14R 18L 25C 27A 38V 60R 73F 106L 115R 117D, relative to SEQ 3. In addition to possessing a unique single fluorescent label, BL22P1B11 (SEQ ID NO: 35) has an exceptionally large affinity for bilirubin ($K_d$=16 nM) and reveals virtually complete quenching of the acrylodan fluorescence ($Q_s$=0.006) at bilirubin saturation of the probe (FIG. 3). BL22P1B11 (SEQ ID NO: 35) has virtually no response to fatty acids, $K_d$s for the most abundant FFA range from 3 to 75 µM (Table 1). Also similarly to L24P19C7 (SEQ ID NO: 36), BL22P1B11 (SEQ ID NO: 35) detects only bilirubin in human plasma and [$B_f$] determined by BL22P1B11 (SEQ ID NO: 35) is consistent with the variation expected from bilirubin-albumin equilibrium in bilirubin spiked plasma (for example see FIG. 5).

Example 4

Figure 4:
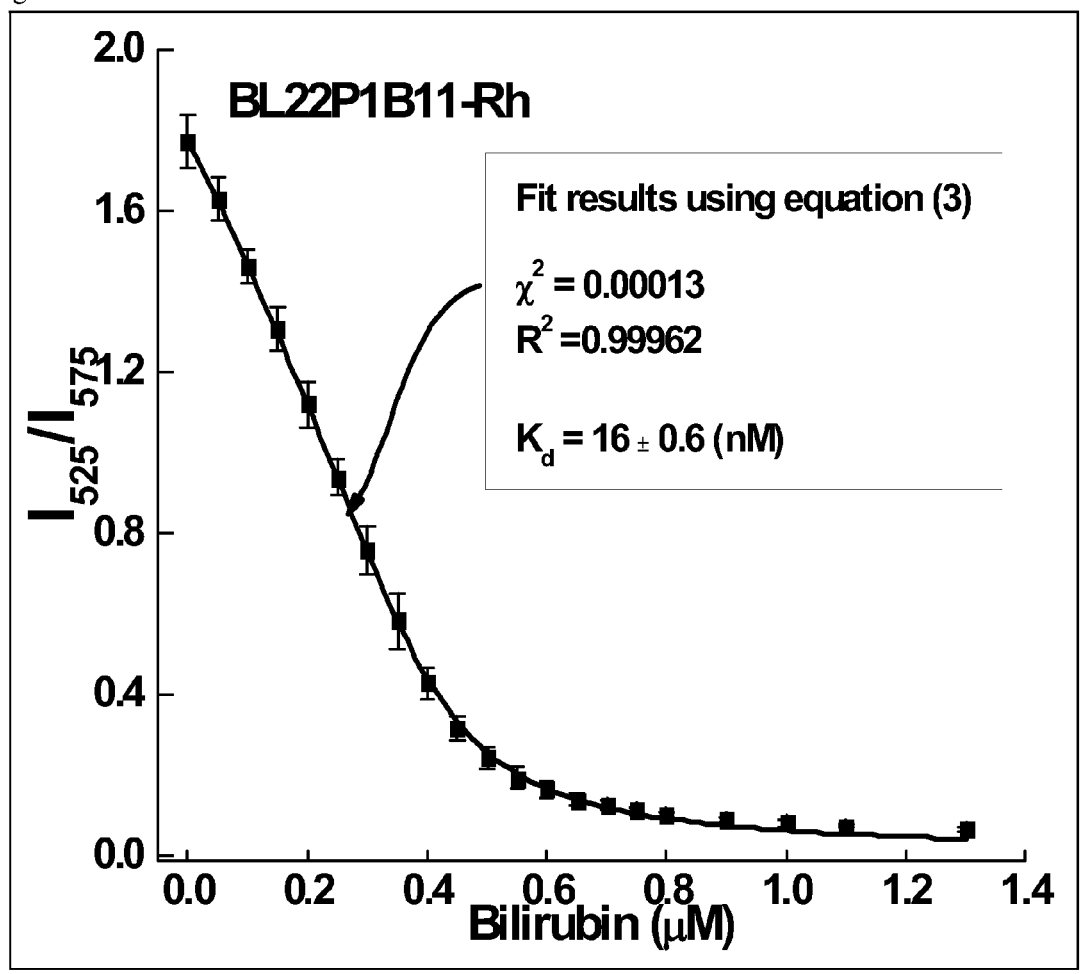
FIG. 4 shows calibration of the BL22P1B11 (SEQ ID NO: 35)-Rh probe carried out by measuring the $I_{525}/I_{575}$ ratio with increasing total bilirubin. Fitting the titration curve with equation (3) is used to determine Kd.

Bilirubin Ratio Probes BL22P1B11 (SEQ ID NO: 35)-Rh and BL22P1B11 (SEQ ID NO: 35)-Dextran-Texas Red BL22P1B11 (SEQ ID NO: 35) provides accurate [$B_f$] values in aqueous solutions including human blood samples, for samples with low total bilirubin. However, with increasing total bilirubin concentrations, the excitation and emission inner filter absorbance due to bilirubin can increase significantly (equation (1)) and therefore without a precise knowledge of the total bilirubin concentration and the absorption geometry ("d" in equation (1)), the apparent [$B_f$] may be significantly in error. To overcome this source of uncertainty and to eliminate the need for determining the total bilirubin concentration, a ratio form of the single wavelength probes such as BL22P1B11 (SEQ ID NO: 35) is used. This is accomplished by adding a second fluorophore that is excited at the same wavelength as the single wavelength probe and whose emission is at a different wavelength than the single wavelength probe. For BL22P1B11 (SEQ ID NO: 35) labeled with acrylodan, an appropriate water soluble fluorophore is Rhodamine B, which can be excited at a similar wavelength as acrylodan, for example 375 nm, and whose emission is significantly longer than acrylodan so that Rhodamine fluoresces at 575 nm and contributes negligibly to the acrylodan fluorescence at 525 nm. Therefore the measurement of the 1525/1575 ratio of intensities is used to determine [Bf] (equation (5)). Because the excitation inner filter absorbance due to bilirubin is the same for acrylodan and Rhodamine B and because the 1525 and 1575 intensities always appear as ratios, the excitation inner filter absorbance does not affect [Bf] measurements, so long as bilirubin absorbance allows sufficient transmission, which can almost always be achieved by reducing pathlength "d" sufficiently. In addition to eliminating excitation inner filter absorbance due to bilirubin, measurements of the ratio of intensities at 525 and 575 nm effectively eliminates emission inner filter due to hemoglobin and bilirubin. This type of ratio probe is prepared by mixing BL22P1B11 (SEQ ID NO: 35) together with Rhodamine B at a defined molecular ratio and then lyophilizing the mixture for storage at −20° C. or lower or is prepared and stored as a solution at 4° C. In either case determination of Ro, the fluorescence ratio in the absence of bilirubin accurately determines the BL22P1B11 (SEQ ID NO: 35)/Rhodamine B molecular ratio. Calibration of the BL22P1B11 (SEQ ID NO: 35)-Rh probe is carried out by measuring the 1525/1575 ratio with increasing total bilirubin. Fitting the titration curve with equation (3) is used to determine Kd and as the results shown in FIG. 4 demonstrate that the Kd (16 nM) of the BL22P1B11 (SEQ ID NO: 35)-Rh probe is identical to that of BL22P1B11 (SEQ ID NO: 35) indicating that the presence of Rhodamine has no effect on the bilirubin-probe interaction.

Figure 9:
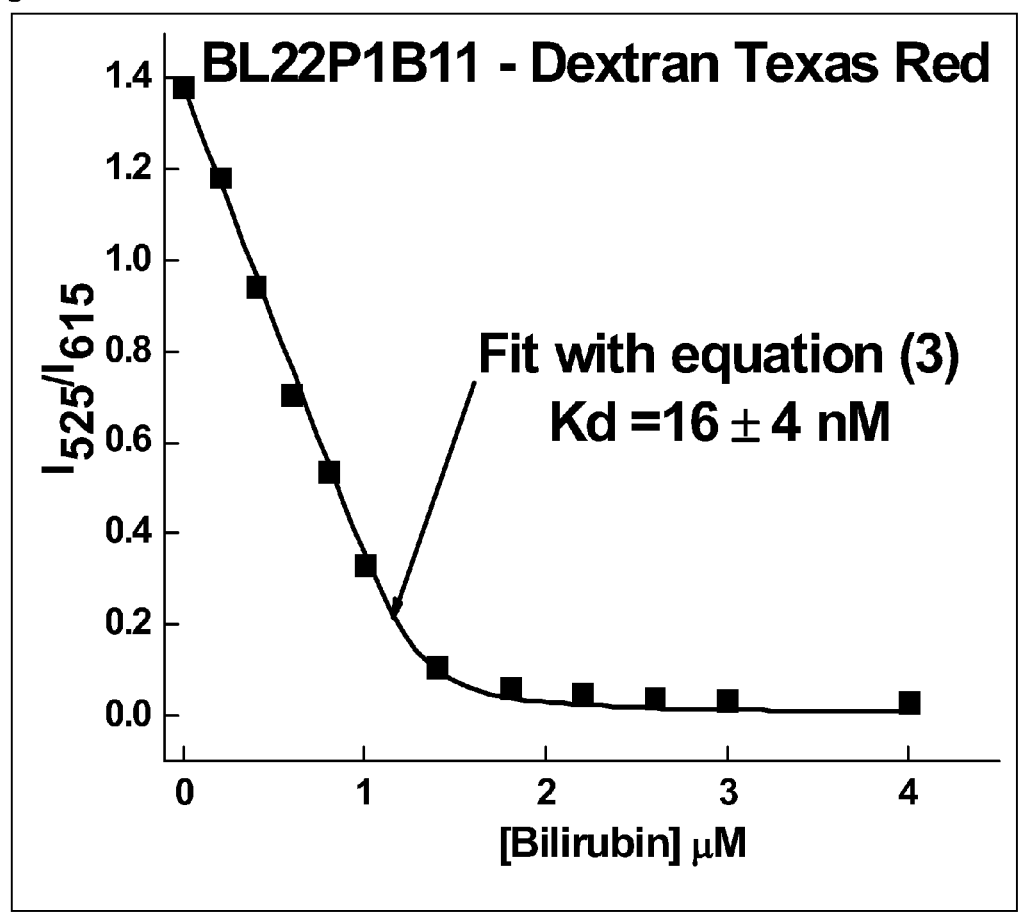
FIG. 9 shows the calibration of the BL22P1B11 (SEQ ID NO: 35)-Dextran-Texas Red probe carried out by measuring the $I_{525}/I_{615}$ ratio with increasing total bilirubin. Fitting the titration curve with equation (3) is used to determine the Kd.

A ratio probe was also generated by mixing BL22P1B11 (SEQ ID NO: 35) together with defined amounts of Texas Red® labeled dextran (Life Technologies, D-3329). The new ratio probe was calibrated and lyophilized (FIG. 9) and calibrated after re-suspension in HEPES buffer. Calibration was carried out by measuring the 1525/1615 ratio with increasing total bilirubin. As observed in FIG. 9, the Kd for the BL22P1B11 (SEQ ID NO: 35)-Dextran Texas Red ratio probe is 16 nM, which is the same as for BL22P1B11 (SEQ ID NO: 35) and BL22P1B11 (SEQ ID NO: 35)-Rh. Thus, a secondary fluorophore can be free in solution (BL22P1B11 (SEQ ID NO: 35)-Rh) or attached to a larger, inert polymer (BL22P1B11 (SEQ ID NO: 35)-Dextran Texas Red) without significantly altering probe-bilirubin interactions.

Figure 5:
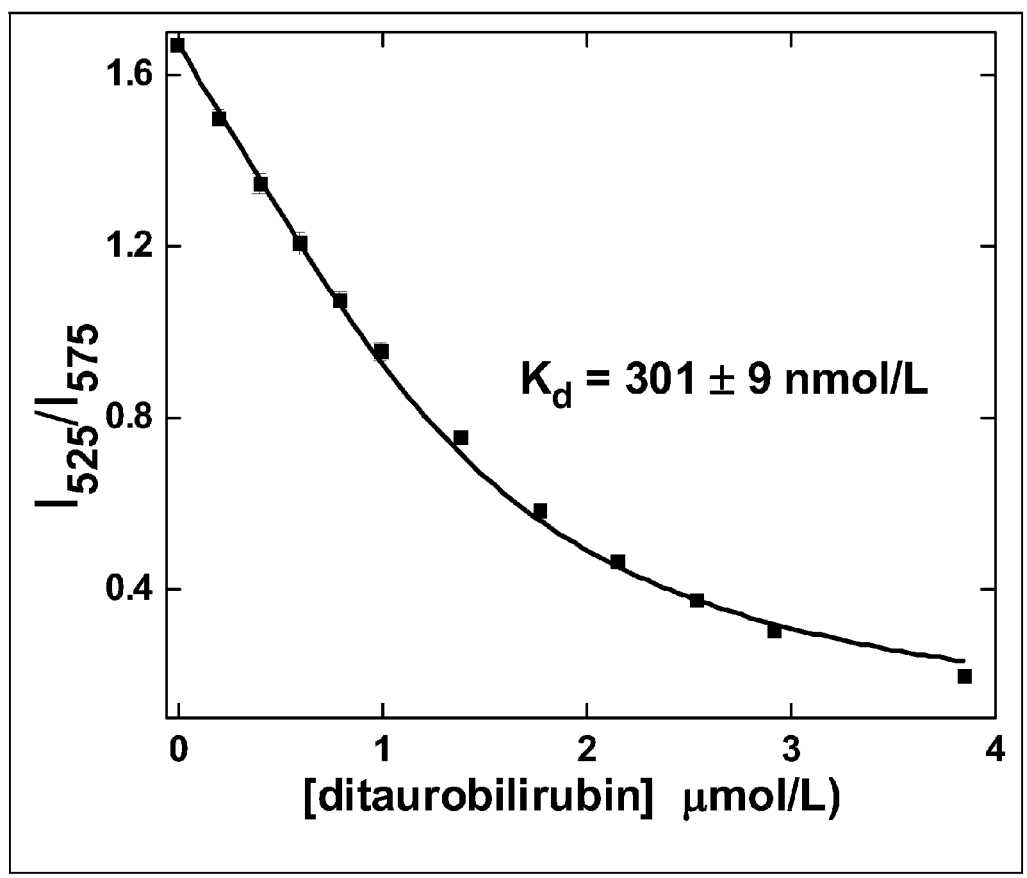
FIG. 5 shows that binding of ditaurobilirubin ($K_d$=300 nM), a model for conjugated bilirubin, to the bilirubin probe BL22P1B11 (SEQ ID NO: 35)-Rh, is about 19 fold weaker than for the binding of unconjugated bilirubin ($K_d$=16 nM).

The potential interference of conjugated bilirubin with the bilirubin probes was estimated by measuring the binding affinity of ditaurobilirubin for BL22P1B11 (SEQ ID NO: 35)-Rh. The measurement was performed by measuring the change in fluorescence response of BL22P1B11 (SEQ ID NO: 35)-Rh titrated with increasing concentrations of ditaurobilirubin. R-values were calculated for all concentrations and the binding isotherm was fitted with equation (3) to obtain a $K_d$ of 301±9 nmol/L for ditaurobilirubin binding to BL22P1B11 (SEQ ID NO: 35)-Rh (FIG. 5).

The effect of photobleaching (photo-oxidation and/or photo-isomerization) on the determination of $B_f$ using the bilirubin probes was evaluated by measuring $B_f$ with BL22P1B11 (SEQ ID NO: 35)-Rh in samples from solutions of bilirubin that had been exposed to light at 460 nm for increasing times. The $B_f$ values were determined using equation (6). Total bilirubin concentrations ($B_T$) were calculated using the measured R values with equation (6).

$$B_T = K_d\left(\frac{(R-R_o)}{(RrR_o-R)}\right) + \frac{P_T K_d\left(\frac{(R-R_o)}{(RrR_o-R)}\right)}{K_d + K_d\left(\frac{(R-R_o)}{(RrR_o-R)}\right)} \quad (6)$$

Figure 6:
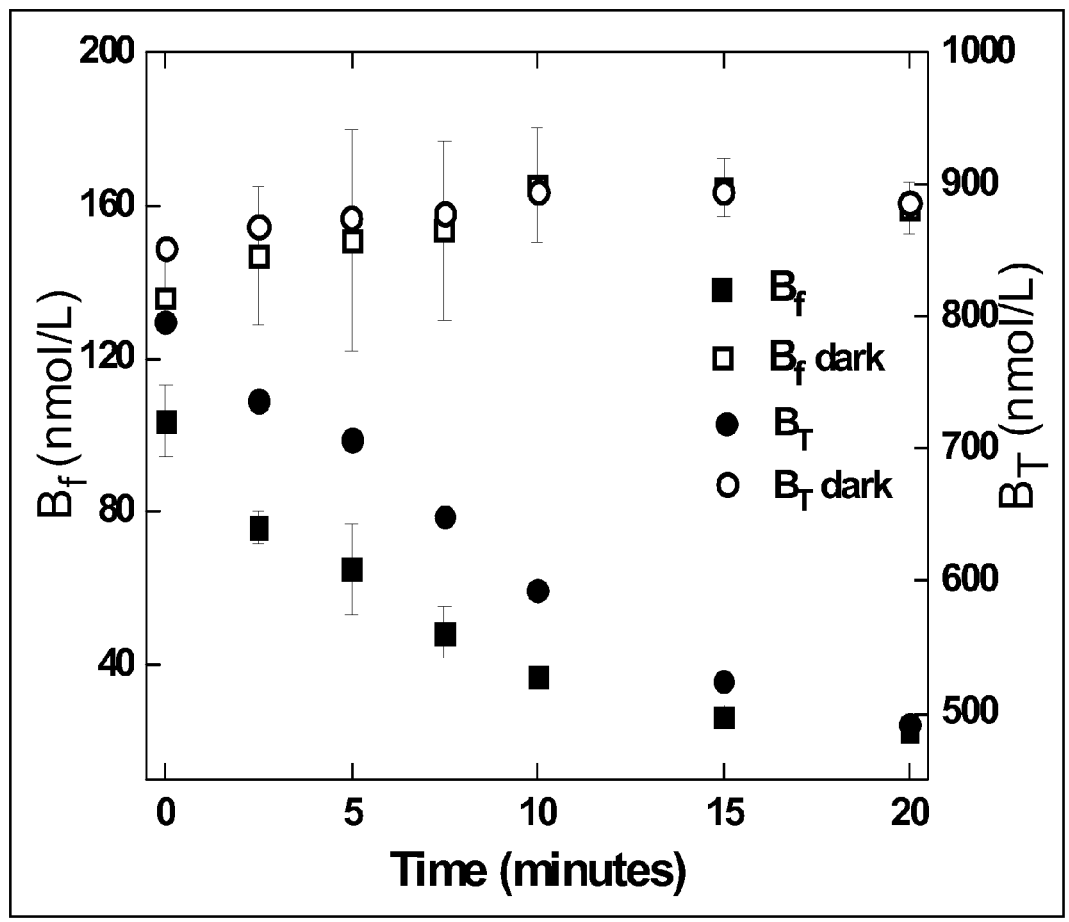
FIG. 6 shows that BL22P1B11 (SEQ ID NO: 35)-Rh monitors the decrease in unbound bilirubin with increasing exposure of bilirubin to 460 nm irradiation. This implies that BL22P1B11 (SEQ ID NO: 35)-Rh is insensitive to the presence of photo-oxidation products and photoisomers of bilirubin that are produced upon 460 nm radiation and should therefore provide a method for accurately monitoring the effectiveness of phototherapy for treating bilirubin toxicity.

The results show that $B_f$ decreased by 78% (FIG. 6) and indicate that BL22P1B11 (SEQ ID NO: 35)-Rh has little or no sensitivity to either the photo-oxidation or the more abundant photo-isomerization products.

Example 5

Figure 7:
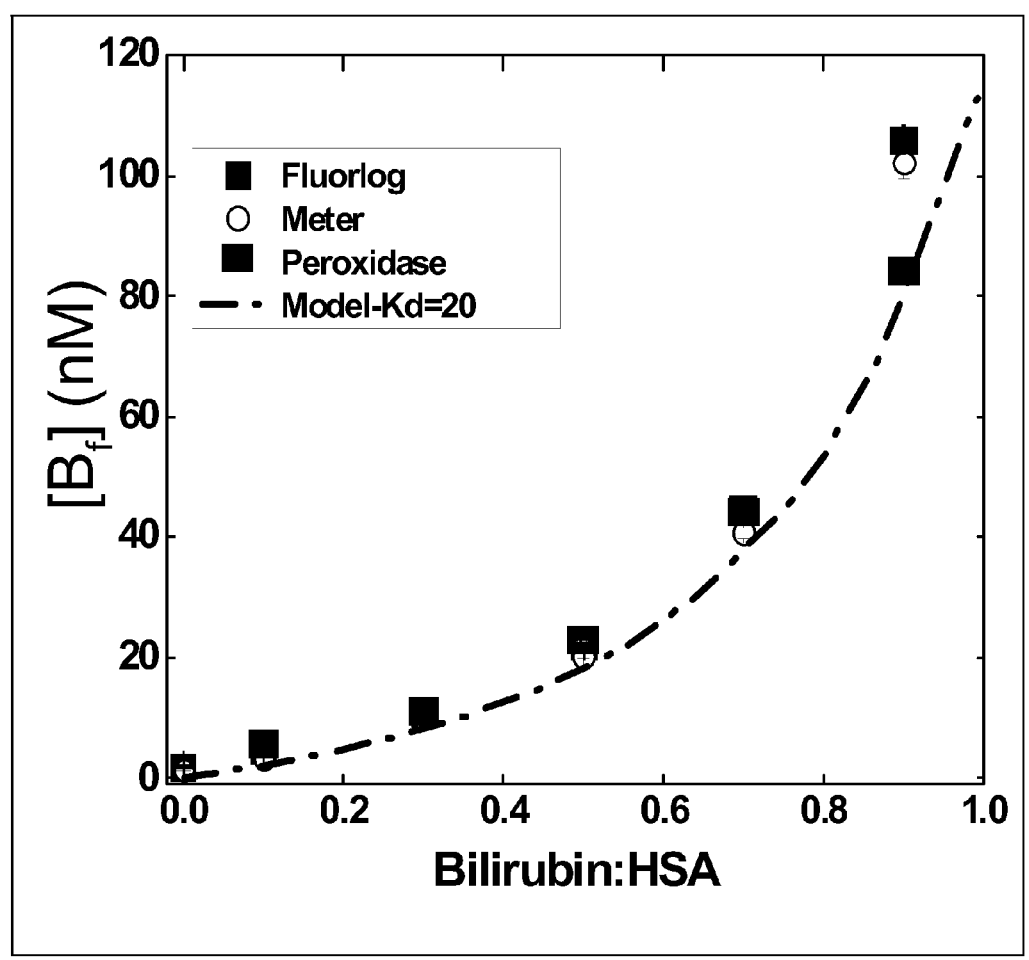
FIG. 7 shows measurements of [Bf] carried out using BL22P1B11 (SEQ ID NO: 35)-Rh in either a Fluorolog3 (J Y Horiba) (♦) using 10×10 mm cuvettes or in a FFAu Meter (FFA Sciences) (○) modified for measuring unbound bilirubin by replacing emission filters with ones centered at 525 and 580 nm. Measurements of [Bf] were also performed on the same samples using the peroxidase method of [Jacobsen J and Wennberg R P. Determination of unbound bilirubin in the serum of newborns. *Clin Chem* 20: 783, 1974] (▲). The results indicate virtually identical results for all 3 measurements and good agreement of the measured and results predicted for bilirubin binding to a single human albumin site with a Kd=20 nM.

Measurement of [$B_f$] in Bilirubin Spiked Human Plasma With BL22P1B11 (SEQ ID NO: 35)-Rh Pooled human plasma (Golden West Biologicals) for which [albumin] was 620 μM was spiked with bilirubin to generate plasma samples with bilirubin/albumin ratios from of approximately 0 to 0.9. Measurements of [Bf] were carried out using BL22P1B1-Rh in either a Fluorolog3 (J Y Horiba) using 10×10 mm cuvettes or in a FFAu Meter (FFA Sciences) modified for measuring unbound bilirubin by replacing emission filters with ones centered at 325 and 380 nm. Measurements of [Bf] were also performed on the same samples using the peroxidase method of Jacobsen and Wennberg [Jacobsen J and Wennberg R P. Determination of unbound bilirubin in the serum of newborns. *Clin Chem* 20: 783, 1974]. The results indicate virtually identical results for all 3 measurements and good agreement of the measured and results predicted for bilirubin binding to a single human albumin site with a Kd=20 nM (FIG. 7). These results demonstrate that the response of the bilirubin probes is entirely due to the interaction with bilirubin, the bilirubin probes are not responsive to other metabolites present in human blood samples. Moreover, the agreement with the peroxidase method and with the predictions of bilirubin-albumin equilibrium also demonstrates that the probes yield accurate unbound bilirubin concentrations.

Example 6

Examples of Labeling Beads, and Dissociation and Effect on $B_f$ Measurements

Bilirubin probe mutants were generated for labeling optimization with Alexa Fluor 680 and LI-COR 700DX and immobilization onto polystyrene or latex beads. Mutants were derived from bilirubin probe, BL22P1B11 (SEQ ID NO: 35), for labeling with fluorescent dyes suitable for use with a plasma or whole blood bilirubin assay. The Alexa Fluor 680 dye was tested on mutants containing a single cysteine at various labeling positions, labeling at position 25C exhibited maximum fluorescence quenching (~40%) upon bilirubin binding. For probe immobilization on polystyrene or latex beads, mutants were developed with single or multiple reactive lysine residues opposite to the Alexa Fluor 680 dye at position 25C (Table 6). In a preferred embodiment LI-COR 700DX (LI-COR Biosciences), was used to label mutants containing a single lysine at various labeling positions and labeling at position 25K exhibited maximum fluorescence quenching (>60%) upon bilirubin binding (Table 6). For probe immobilization on polystyrene or latex beads, mutants were developed with single or multiple reactive cysteine residues opposite to the LI-COR 700DX dye at position 25K. Further improvement for immobilization was achieved using two affinity based methods, double His-tags and PS-tags (polystyrene binding peptide) to immobilize the LI-COR 700DX-labeled bilirubin probe onto polystyrene or latex beads (Table 8). One mutant (BL22P1B11 (SEQ ID NO: 35)_25K_C2X) with C-terminal double his-tags separated by a linker consisting of 11 amino acid residues (SRAWRHPQFGG (SEQ ID NO: 28)) was found to have high binding affinity to Ni-coupled Dyna polystyrene or latex beads (Life Technologies) and acceptable quenching by bilirubin (~50%). Another mutant (BL22P1B11 (SEQ ID NO: 35)_25K_PS19) with a PS-tag (PS19-1, RAFIASRRIRRP (SEQ ID NO: 29)) immediately after the His-tag at its C-terminus also showed higher affinity than the template with a single His-tag (BL22P1B11 (SEQ ID NO: 35)_25K). Other PS tags that produced probes that bound to the polystyrene or latex beads with high affinity included PS19-6L (RLLLRRLRR (SEQ ID NO: 30)) and PS19-6I (RIIIRRIRR (SEQ ID NO: 41)) (Table 8). Furthermore, the BL22P1B11 (SEQ ID NO: 35)_25K_PS19 probe exhibited the highest bilirubin quenching both in free solution and on beads (>60%), presumably due the presence of the additional PS-tag. Both probes generated a bilirubin quenching curve similar to the one from a standard fluorometer.

In a more preferred embodiment a bilirubin mutant probe was generated by constructing and screening a linker library based on a LI-COR 700DX-labeled BL22P1B11 (SEQ ID NO: 35)_25K_C2X template (Table 8). The new mutant probe has higher protein expression; no multiple labeling, little or no amine labeling at N-terminus, higher probe yield and high affinities for the polystyrene or latex beads. For example (Table 4) approximately 12% of the PS19 probe dissociates from the beads after 60 min incubation in a HEPES buffer such as described in [Huber A H, Kampf J P, Kwan T, Zhu B and Kleinfeld A M. Fatty acid-specific fluorescent probes and their use in resolving mixtures of different unbound free fatty acids in equilibrium with albumin. *Biochemistry* 45: 14263-14274, 2006]. This dissociated probe accounts for approximately 60% of the total fluorescence intensity (Table 4). The C2XFFA3P1H11 probe has a unique 3-amino acid linker (AAS) which was inserted between BL22P1B11 (SEQ ID NO: 35)_25K and the first His-tag, and a novel 11-amino acid (SHRATPNTSPH (SEQ ID NO: 32)) linker between the first and second His-tag replaced the original linker in BL22P1B11 (SEQ ID NO: 35)_25K_C2X. Testing of both clones showed significant improvement over PS19 and BL22P1B11 (SEQ ID NO: 35)_25K_C2X (Tables 2-4). Both mutants have the following properties that make them the ideal choice for large-scale probe production and commercialization. High protein expression yield, low reactivity or accessibility of N-terminal amine by 700DX, high probe yield with ~100% eluted from Ni-beads with EDTA after labeling, high bilirubin quenching equivalent or better that PS19, the same probe bilirubin quenching of the 700DX fluorescence for the probe immobilized on polystyrene or latex beads as in free solution, 10 times higher bead affinity than PS-19 (~5% free probe intensity vs. ~60%) and unique linkers and spacers.

Time courses of C2XFFA3H11, C2XFFA3B3, and PS19 immobilized on Ni-coupled Dyna polystyrene or latex beads were carried out on two different days and are shown in Tables 2-4 in which bilirubin quenching of the LiCor 700Dx fluorescence was mediated by bilirubin-albumin complexes at total bilirubin/albumin of approximately 0.9.

TABLE 2

C2XFF3H11-700DX

|  | Time (minutes) | % quench | Supernatant Intensity as % of total |
|---|---|---|---|
| C2XFFA3H11 | 0 | 24.21% |  |
|  | 4 | 49.14% |  |
|  | 8 | 51.47% |  |
|  | 15 | 54.60% |  |
|  | 30 | 56.81% |  |
|  | 60 | 58.14% |  |
|  | 60S | 58.97% | 4.6% |

TABLE 3

C2XFFA3B3-700DX

|  | Time (minutes) | % quench | Supernatant Intensity as % of total |
|---|---|---|---|
| C2XFFA3B3 | 0 | 21.14% |  |
|  | 4 | 42.06% |  |
|  | 8 | 45.12% |  |
|  | 15 | 48.67% |  |
|  | 30 | 50.70% |  |
|  | 60 | 50.23% |  |
|  | 60S | 61.26% | 7.8% |

TABLE 4

PS19-1-700DX

|  | Time (minutes) | % quench | Supernatant Intensity as % of total |
|---|---|---|---|
| PS19-1 | 0 | 29.46% |  |
|  | 4 | 47.36% |  |
|  | 8 | 50.46% |  |
|  | 15 | 54.06% |  |
|  | 30 | 53.74% |  |
|  | 60 | 55.30% |  |
|  | 60S | 49.23% | 61.5% |

Example 7

Figure 8:
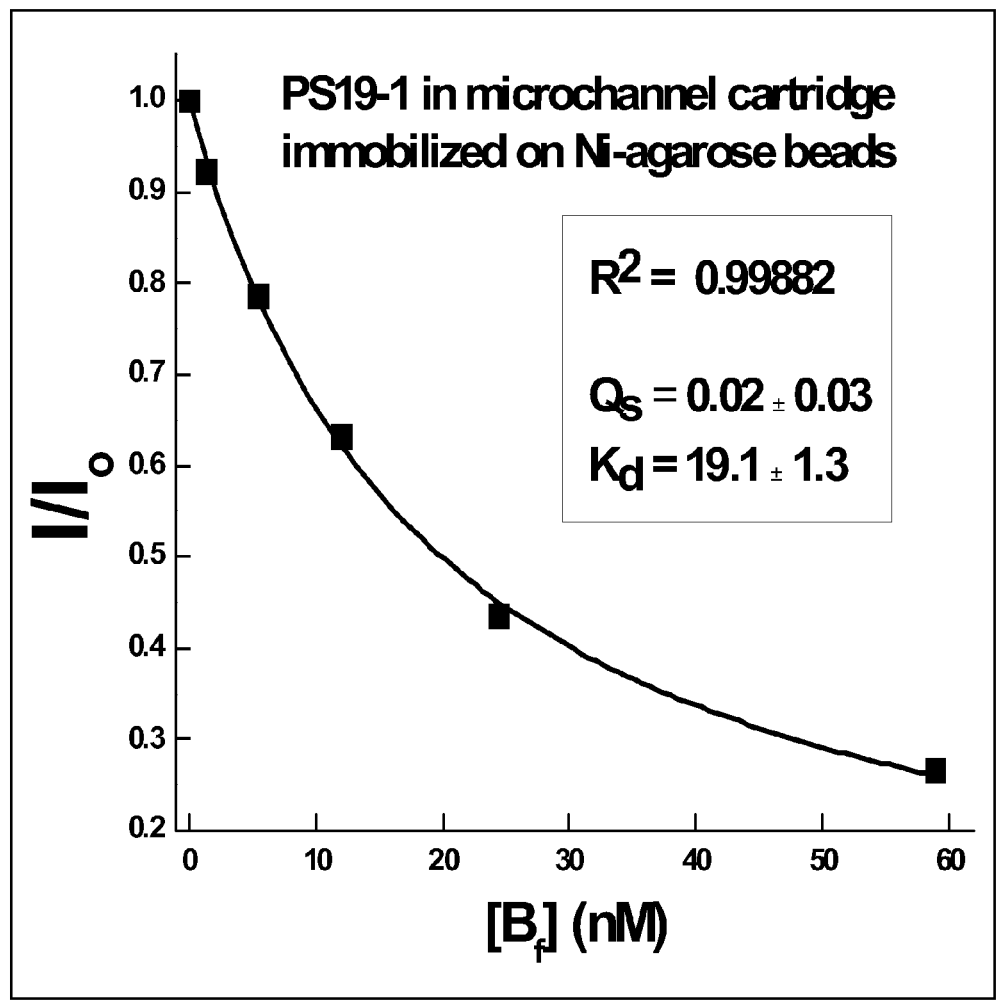
FIG. 8 shows bilirubin quenching results for the probe PS19-1 immobilized on Ni-agarose beads immobilized in a "well" of a set of microchannel disposable cartridges designed for fluorometric measurements. Bilirubin spiked adult human blood plasma samples of 20 μL, undiluted, were added to the cartridges and quenching of the DX700 fluorescence by unbound bilirubin was fit to the data using equation (5) to determine the $K_d$.

Measurements of Spiked Plasma with Immobilized Bilirubin Probes in a Disposable Cartridge The probe PS19-1 which is BL22P1B11 (SEQ ID NO: 35)_25K labeled with LiCor DX700 and with, in addition to the 6×His tag, has a PS-tag, RAFIASRRIRRP at the C-terminus (Table 8), was immobilized on Ni-agarose beads. These labeled beads were in turn immobilized in a "well" of a set of microchannel disposable cartridges designed for fluorometric measurements. Bilirubin spiked adult human blood plasma samples of 20 µL, undiluted, were added to the cartridges and quenching of the DX700 fluorescence by unbound bilirubin was determined for samples with increasing $[B_f]$ values. These measurements were used to determine the $K_d$ of the immobilized PS19-1 and to evaluate reproducibility of the bilirubin probes in such cartridges. The $K_d$ determined from these measurements is consistent with the value obtained from the free BL22P1B11 (SEQ ID NO: 35)-Rh probe (FIG. 8) indicating that immobilization does not affect the equilibrium between the probe and the bilirubin-albumin interaction. Moreover, virtually the same results were obtained using cartridges that were stored for more than 2 months after preparation.

Example 8

Single Cysteine Probes

TABLE 5

All residue numbers refer to SEQ ID 3, the template sequence.

| Construct | Primary Fluor | Kd | Is | Mutations |
|---|---|---|---|---|
| L2P14F7 | Texas Red C2-Maleimide |  |  | 18G 27C 31M 72A |
| L2P14 F7 - K27C | Acrylodan | 250 | 0.02 | 18G 27C 31M 72A |
| L2P14 F7 - KR14 - K27C | Acrylodan | 530 | 0.16 | KR14 -18G 27C 31M 72A |
| L2P14F7 MGCFD KR14 | Acrylodan |  |  | MGCFD - KR14 - 18G 31M 72A |
| L2P14F7 MGCFD KR14 | DACIA |  |  | MGCFD - KR14 - 18G 31M 72A |
| L2P14F7 MGCFD KR14 | Lucifer Yellow iodoacetamide |  |  | MGCFD - KR14 - 18G 31M 72A |
| L2P14F7 MGCFD KR14 | Texas Red C2-Maleimide |  |  | MGCFD - KR14 - 18G 31M 72A |
| L2P14F7-MGCFD | Texas Red C2-Maleimide | 400 | 0.3 | MGCFD - 18G 31M 72A |
| L2P14F7 MGI KR14 K27C | Acrylodan | 350 | 0 | MGI - KR14 - 18G 27C 31M 72A |
| L10P9 E6 | Acrylodan | 1432 | 0.1 | 14T 18L 73M 117C 72A |
| L22P19 B9 | Acrylodan | 400 | 0 | 38R 72A 73M 106Q 115C |
| L22P33 A10 | Acrylodan | 245 | 0.045 | 38R 72A 73N 106S 115C |
| L24P19 C7 | Acrylodan | 35 | 0.03 | 14R 18L 38V 60R 73F 106C 115R 117D |
| L24P19 C7 | Alexa Fluor 680 C2-maleimide |  |  | 14R 18L 38V 60R 73F 106C 115R 117D |
| L24P19 C7 | Kodak X-Sight 670 LSS dye |  |  | 14R 18L 38V 60R 73F 106C 115R 117D |
| L24P19 C7 | Texas Red C2-Maleimide |  |  | 14R 18L 38V 60R 73F 106C 115R 117D |
| L24P19C7- K27C | Acrylodan | 242 | 0.067 | 14R 18L 27C 38V 60R 73F 106C 115R 117D |
| L24P19C7- K27C - R106A | Acrylodan |  |  | 14R 18L 27C 38V 60R 73F 106A 115R 117D |
| L24P19 C7- KR14 | Acrylodan |  |  | KR14 - 14R 18L 38V 60R 73F 106C 115R 117D |
| L24P19C7 - KR14 - K27C | Acrylodan |  |  | KR14 - 14R 18L 27C 38V 60R 73F 106C 115R 117D |
| L24P19 C7 K27A | Acrylodan | 21 | 0.011 | 14R 18L 27A 38V 60R 73F 106C 115R 117D |

TABLE 5-continued

All residue numbers refer to SEQ ID 3, the template sequence.

| Construct | Primary Fluor | Kd | Is | Mutations |
|---|---|---|---|---|
| L24P19 C7 K27K 22C | Acrylodan | 71 | 0.06 | 14R 18L 22C 38V 60R 73F 106C 115R 117D |
| L24P19 C7 K27K 24C | Acrylodan | 89 | 0.02 | 14R 18L 24C 38V 60R 73F 106C 115R 117D |
| L24P19 C7 K27K 25C | Acrylodan | 19 | 0.02 | 14R 18L 25C 38V 60R 73F 106C 115R 117D |
| L24P19 C7 K27K 26C | Acrylodan | 19 | 0.02 | 14R 18L 26C 38V 60R 73F 106C 115R 117D |
| L24P19 C7 K27K 30C | Acrylodan | 26 | 0.03 | 14R 18L 30C 38V 60R 73F 106C 115R 117D |
| L24P19 C7-K27A-MGCFD | Texas Red C2-Maleimlde | | | MGCFD - 14R 18L 27A 38V 60R 73F 106C 115R 117D |
| L24P19 C7-MGCFD | Texas Red C5-Bromoacetamide | | | MGCFD - 14R 18L 38V 60R 73F 106C 115R 117D |
| L24P19 C7-MGCFD | Texas Red C2-Maleimide | | | MGCFD - 14R 18L 38V 60R 73F 106C 115R 117D |
| L24P19C7 - KR6 | Acrylodan | | | KR6 - 14R 18L 38V 60R 73F 106C 115R 117D |
| L45P2 E10 | Acrylodan | | | 18E 23L 31N 72G 73T 74A 78Y 102C 106W 115W 117L |
| BL2P2 B6 | Acrylodan | 137 | 0.05 | 14R 18L 31C 38V 60R 73V 106A 115R 117D |
| BL10P10 D10 | Acrylodan | 400 | 0.15 | 14F 18L 27C 38M 60Y 73F 106V 115R 117D |
| BL10P14 E1 | Acrylodan | | | 14F 18L 27C 38S 60D 73F 106I 115R 117S |
| BL10P19 F8 | Acrylodan | | | 14M 27C 38F truncated after 44 |
| BL10P23 H9 | Acrylodan | >50 | 0.16 | 14R 27C 38I 60Y 73F 106V 115R 117D |
| BL10P25 E7 | Acrylodan | 35 | 0.19 | 14F 18L 27C 60R 73F 106V 115R 117D |
| BL10P25E7 - KR14 | Acrylodan | 35 | ~0 | KR14 - 14F 18L 27C 60R 73F 106V 115R 117D |
| BL10P26E7 - MGI - KR14 | Acrylodan | 19 | 0 | MGI - KR14 - 14F 18L 27C 60R 73F 106V 115R 117D |
| BL10P8 D3 | Acrylodan | 1033 | 0 | 14G 18L 27C 38M 60Y 73F 106I 115R 117D |
| BL22P1 B11 | Acrylodan | 16 | 0 | MGI - KR14 - 14R 18L 25C 27A 38V 60R 73F 106L 115R 117D |
| BL22P1 B11 | Alexa Fluor 750 C5-maleimide | | | MGI - KR14 - 14R 18L 25C 27A 38V 60R 73F 106L 115R 117D |
| BL22P1 B11 | BODIPY 577/618 | | | MGI - KR14 - 14R 18L 25C 27A 38V 60R 73F 106L 115R 117D |
| BL22P1 B11 | Alexa Fluor 680 C2-maleimide | 110 | 0.37 | MGI - KR14 - 14R 18L 25C 27A 38V 60R 73F 106L 115R 117D |
| BL22P1 B11 - 130K | Acrylodan | | | MGI - KR14 - 14R 18L 25C 27A 38V 60R 73F 106L 115R 117D 130K |
| BL22P1B11 - 7K | Alexa Fluor 680 C2-maleimide | | | MGI - KR14 - 7K 14R 18L 25C 27A 38V 60R 73F 106L 115R 117D |
| BL22P1B11 - MGGSATGIFD | Acrylodan | | | MGGSATGIFD- KR14 - 14R 18L 25C 27A 38V 60R 73F 106L 115R 117D |
| BL22P1 B11 - 24C | Alexa Fluor 680 C2-maleimide | 72 | 0.41 | MGI - KR14 - 14R 18L 24C 27A 38V 60R 73F 106L 115R 117D |
| BL22P1 B11 - 26C | Alexa Fluor 680 C2-maleimide | 197 | 0.43 | MGI - KR14 - Y14R M18L V26C K27A L38V V60R A73F R106L Q115R Y117D |
| BL22P1 B11 - 27C | Alexa Fluor 680 C2-maleimide | 70 | 0.4 | MGI - KR14 - Y14R M18L K27C L38V V60R A73F R106L Q115R Y117D |
| BL22P1 B11 - 27C | Alexa Fluor 750 C5-maleimide | 154 | 0.66 | |
| BL22P1 B11 - 29C | Alexa Fluor 680 C2-maleimide | 118 | 0.65 | MGI - KR14 - 14R 18L 27A 29C 38V 60R 73F 106L 115R 117D |
| BL22P1 B11 - 30C | Alexa Fluor 680 C2-maleimide | | | MGI - KR14 - 14R 18L 27A 30C 38V 60R 73F 106L 115R 117D |
| BL22P1 B11 - 33C | Alexa Fluor 680 C2-maleimide | 250 | 0.45 | MGI - KR14 - 14R 18L 27A 33C 38V 60R 73F 106L 115R 117D |
| BL22P1 B11 - 33C | Alexa Fluor 750 C5-maleimide | 120 | 0.3 | |
| BL22P1 B11 - 54C | Alexa Fluor 680 C2-maleimide | 160 | 0.52 | MGI - KR14 - 14R 18L 27A 38V 54C 60R 73F 106L 115R 117D |
| BL22P1 B11 - 54C | Alexa Fluor 750 C5-maleimide | | | |
| BL22P1 B11 - 74C | Alexa Fluor 680 C2-maleimide | 160 | 0.5 | MGI - KR14 - 14R 18L 27A 38V 60R 73F 74C 106L 115R 117D |
| BL22P1 B11 - 76C | Alexa Fluor 680 C2-maleimide | 150 | 0.24 | MGI - KR14 - 14R 18L 27A 38V 60R 73F 76C 106L 115R 117D |
| BL22P1 B11 - 76C | Alexa Fluor 750 C5-maleimide | 140 | 0.55 | |
| BL22P1B11 - 97C | Alexa Fluor 680 C2-maleimide | 100 | 0.5 | MGI - KR14 - 14R 18L 27A 38V 60R 73F 97C 106L 115R 117D |
| BL22P1B11 - 98C | Alexa Fluor 680 C2-maleimide | | | MGI - KR14 - 14R 18L 27A 38V 60R 73F 98C 106L 115R 117D |
| BL22P1 B11 - 27C | Alexa Fluor 750 C5-maleimide | 154 | 0.66 | |
| BL22P1 B11 - 33C | Alexa Fluor 750 C5-maleimide | 120 | 0.3 | |
| BL22P1 B11 - 54C | Alexa Fluor 750 C5-maleimide | | | |
| BL22P1 B11 - 76C | Alexa Fluor 750 C5-maleimide | 140 | 0.55 | |
| BL22P2D4 | Acrylodan | | | MGI-14KR-14R 18L 25C 27A 38V 60R 73F 106V 115R 117D |
| BL22P2F3 | Acrylodan | | | MGI-14KR-14R 18L 25C 27A 38V 60R 73F 106V 115R 117D |

Example 9

Single Fluorescently Labeled Lysine Probes

TABLE 6

All residue numbers refer to SEQ ID 3, the template sequence

| Construct | Primary Fluor | Kd | Is | Mutations |
|---|---|---|---|---|
| L1P1 B4 | Acrylodan | 711.3 | 0 | 14I 72W 117W |
| L1P1 C 12 | Acrylodan | 35.75 | 0.11 | 38I 72W 117W |
| L1P12 E8 | Acrylodan | | | 14L 38A 72G 117F 114E |
| L1P14 D6 | Acrylodan | 308.7 | 0.04 | 14M 72V 117W |
| L1P5 H9 | Acrylodan | | | 14M 72I 117W |
| L2P14 F7 | Acrylodan | 69.03 | 0.01 | 18G 31M 72A |
| L2P14F7 MGI KR14 K27K | Acrylodan | 84 | 0.00 | MGI - KR14 - 18G 27K 31M 72A |

TABLE 6-continued

All residue numbers refer to SEQ ID 3, the template sequence

| Construct | Primary Fluor | Kd | Is | Mutations |
|---|---|---|---|---|
| L2P22 B1 | Acrylodan | | | 18Y 31V 55V 72A |
| L5P16 H4 | Acrylodan | 350 | 0.00 | 126K 73F 72A |
| L10P1 H5 | Acrylodan | 432 | 0.04 | 14H 18L 31N 73S 117A 72A |
| L10P11 B9 | Acrylodan | 730 | 0.00 | 14H 18L 31R 73H 117V 72A |
| L10P19 C1 | Acrylodan | 471 | 0.04 | 14L 18F 31R 72A 73L 131D |
| L10P20 D8 | Acrylodan | 229 | 0.09 | 14A 18F 31L 73V 117L 72A |
| L14P7 G4 | Acrylodan | 484 | 0.19 | 36A 38V 72A 82V 106A 115A 117M |
| L14P9 G3 | Acrylodan | 667 | 0.27 | 36A 38A 72A 82V 106V 115A 117M |
| L14P10 B11 | Acrylodan | 661 | 0.09 | 36V 38V 72A 82V 106V 115A 117A |
| L14P12 G1 | Acrylodan | 701 | 0.23 | 36V 38A 72A 82A 106A 115A 117I |
| L14P13 A2 | Acrylodan | 1086 | 0.17 | 36I 38A 72A 82V 106A 115V 117T |
| L14P14 E4 | Acrylodan | 713 | 0.17 | 36A 38A 72A 82I 106A 115A 117V |
| L14P15 F3 | Acrylodan | 383 | 0.23 | 36V 38V 72A 106A 115T 117V |
| L14P18 H7 | Acrylodan | 484 | 0.26 | 36V 38A 72A 82V 106A 115T 117M |
| L14P19 H8 | Acrylodan | 435 | 0.15 | 36A 38V 72A 82M 106A 115A 117M |
| L14P20 F5 | Acrylodan | 1339 | 0.21 | 36V 38A 72A 82V 106V 115A 117M |
| L24P12 C8 | Acrylodan | 2 | 0.04 | 14R 18L 38V 60R 73F 115M 117D |
| L24P19 C7 | Acrylodan | 33 | 0.01 | 14R 18L 27A 38V 60R 73F 106A 115R 117D |
| L24P19 C7 | Kodak X-Sight 670 LSS dye | | | |
| L43P11 G2 | Acrylodan | | | 14Q 18L 23L 31N 72G 73T 74A 104K 106W 115W 117S |
| L43P8 H7 | Acrylodan | | | 14L 18L 23L 31N 72G 73T 74A 104R 106W 115W 117W |
| L45P5 E5 | Acrylodan | | | 18S 23L 31N 72G 73T 74A 78V 106W 115W 117L |
| L46P3 A3 | Acrylodan | | | 18L 23R 31N 72G 73T 74A 102H 106W 115W 117L |
| BL1P1 F2 | Acrylodan | | | 14R 18L 38V 60R 73F 106R 115R 117D |
| BL1P2 H2 | Acrylodan | 40 | 0.00 | 14R 18L 38V 60R 73F 106A 115R 117D |
| BL8P12 D3 | Acrylodan | 455 | 0.02 | 38A, 60F, 73F, 106V, 115R, 117D |
| BL8P15 G6 | Acrylodan | 3250 | 0.34 | 18L, 38V, 60Y, 73F, 106D, 115R, 117N |
| BL8P20 G1 | Acrylodan | 476 | 0.10 | 18L, 38T, 60Y, 73F, 106T, 115R, 117S |
| BL8P20 G3 | Acrylodan | 2308 | 0.09 | 18L, 38M, 60H, 73F, 106T, 115R, 117E |
| BL8P21 E8 | Acrylodan | 3216 | 0.28 | 18L 38I 60H 73F 106D 115R 117E |
| BL8P9 C9 | Acrylodan | 723 | 0.00 | 18L, 38F, 60F, 73F, 106D, 115R, 117R |
| BL8PS G9 | Acrylodan | 1050 | 0.29 | 18L, 38A, 73F, 106V, 115R, 117D |
| BL10P20 G4 | Acrylodan | | | 14G 18L 38A 60F 73F 106I 115R 117E |
| BL22P1B11-25K | Biotium CF750 SE | 9500 | 0.19 | MGI - KR14 - 14R 18L 25K 27A 38V 60R 73F 106L 115R 117D |
| BL22P1B11-26K | Biotium CF750 SE | 1225 | 0.60 | MGI - KR14 - 14R 18L 26K 27A 38V 60R 73F 106L 115R 117D |
| BL22P1B11-30K | Biotium CF750 SE | 1230 | 0.60 | MGI - KR14 - 14R 18L 27A 30K 38V 60R 73F 106L 115R 117D |
| BL22P1B11-25K | Kodak X-Sight 670 LSS dye | 700 | 0.61 | MGI - KR14 - 14R 18L 25K 27A 38V 60R 73F 106L 115R 117D |
| BL22P1B11-26K | Kodak X-Sight 670 LSS dye | 260 | 0.50 | MGI - KR14 - 14R 18L 26K 27A 38V 60R 73F 106L 115R 117D |
| BL22P1B11-27K | Kodak X-Sight 670 LSS dye | 5250 | 0.48 | MGI - KR14 - 14R 18L 38V 60R 73F 106L 115R 117D |
| BL22P1B11-29K | Kodak X-Sight 670 LSS dye | 640 | 0.48 | MGI - KR14 - 14R 18L 27A 29K 38V 60R 73F 106L 115R 117D |
| BL22P1B11-30K | Kodak X-Sight 670 LSS dye | 480 | 0.56 | MGI - KR14 - 14R 18L 27A 30K 38V 60R 73F 106L 115R 117D |
| BL22P1 B11 - 25K | LiCor IRDye 680 LT | 239 | 0.67 | MGI - KR14 - 14R 18L 25K 27A 38V 60R 73F 106L 115R 117D |
| BL22P1B11-25K | LiCor IRDye 700DX | 80 | 0.14 | MGI - KR14 - 14R 18L 25K 27A 38V 60R 73F 106L 115R 117D |
| BL22P1B11-26K | LiCor IRDye 700DX | 109 | 0.22 | MGI - KR14 - 14R 18L 26K 27A 38V 60R 73F 106L 115R 117D |

Example 10

Two Fluorophore Bilirubin Probes

TABLE 7

All residue numbers refer to SEQ ID 3, the template sequence.

| Construct | Primary Fluor | Second Fluor | Kd | Qs | Mutations |
|---|---|---|---|---|---|
| Two fluorophores covalently attached to probe ||||||
| L2P14F7 | Acrylodan | Texas Red-X SE | | | 18G 31M 72A |
| L2P14F7 MGCFD KR14 | Acrylodan | Alexa Fluor 594 | | | MGCFD - KR14 - 18G 31M 72A |
| L2P14F7 MGCFD KR14 | Acrylodan | Alexa Fluor 633 | | | MGCFD - KR14 - 18G 31M 72A |
| L2P14F7 MGCFD KR14 | DACIA | Texas Red | | | MGCFD - KR14 - 18G 31M 72A |
| L2P14F7 MGCFD KR14 | Lucifer Yellow iodoacetamide | Texas Red | | | MGCFD - KR14 - 18G 31M 72A |
| L2P14F7-MGCFD | Acrylodan | Texas Red C2-Maleimide | | | MGCFD -18G 31M 72A |
| L24P19 C7-K27A-MGCFD | Acrylodan | Texas Red C2-Maleimide | | | MGCFD - 14R 18L 27A 38V 60R 73F 106C 115R 117D |
| L24P19 C7-MGCFD | Acrylodan | Texas Red C2-Maleimide | | | MGCFD - 14R 18L 38V 60R 73F 106C 115R 117D |
| BL10P25 E7 | Acrylodan | Texas Red-X SE | | | 14F 18L 27C 60R 73F 106V 115R 117D |
| BL10P25E7 - MGI - KR14 | Acrylodan | Texas Red-X SE | | | MGI - KR14 - 14F 18L 27C 60R 73F 106V 115R 117D |

TABLE 7-continued

All residue numbers refer to SEQ ID 3, the template sequence.

| Construct | Primary Fluor | Second Fluor | Kd | Qs | Mutations |
|---|---|---|---|---|---|
| BL10P25E7 - MGI - KR14 | Acrylodan | Rhodamine Red X-SE | | | MGI - KR14 - 14F 18L 27C 60R 73F 106V 115R 117D |
| BL10P25E7 - MGI- KR14 | Acrylodan | Texas Red | | | MGI - KR14 - 14F 18L 27C 60R 73F 106V 115R 117D |
| BL22P1 B11 | Acrylodan | Cascade Yellow - SE | | | MGI - KR14 - 14R 18L 25C 27A 38V 60R 73F 106L 115R 117D |
| BL22P1 B11 | Acrylodan | Dansyl chloride | | | MGI - KR14 - 14R 18L 25C 27A 38V 60R 73F 106L 115R 117D |
| BL22P1 B11 | Acrylodan | Dapoxyl - SE | | | MGI - KR14 - 14R 18L 25C 27A 38V 60R 73F 106L 115R 117D |
| BL22P1 B11 | Acrylodan | Dapoxyl Carboxylic Acid | | | MGI - KR14 - 14R 18L 25C 27A 38V 60R 73F 106L 115R 117D |
| BL22P1 B11 | Acrylodan | NBD-sulfonyl chloride | | | MGI - KR14 - 14R 18L 25C 27A 38V 60R 73F 106L 115R 117D |
| BL22P1 B11 | Acrylodan | Rhodamine Isothiocyanate | | | MGI - KR14 - 14R 18L 25C 27A 38V 60R 73F 106L 115R 117D |
| BL22P1 B11 | Acrylodan | Rhodamine Red X-SE | | | MGI - KR14 - 14R 18L 25C 27A 38V 60R 73F 106L 115R 117D |
| BL22P1 B11 | Acrylodan | SPDP + Rhodamine Red X-SE | | | MGI - KR14 - 14R 18L 25C 27A 38V 60R 73F 106L 115R 117D |
| BL22P1 B11 | Acrylodan | Texas Red-X SE | | | MGI - KR14 - 14R 18L 25C 27A 38V 60R 73F 106L 115R 117D |
| BL22P1 B11 - 130K | Acrylodan | Rhodamine Red X-SE | | | MGI - KR14 - 14R 18L 25C 27A 38V 60RA73F 106L 115R 117D 130K |
| BL22P1 B11 - 130K | Aorylodan | SPDP + Rhodamine Red X-SE | | | MGI - KR14 - 14R 18L 25C 27A 38V 60RA73F 106L 115R 117D 130K |
| BL22P1B11 - MGGSATGIFD | Acrylodan | Rhodamine Red X-SE | | | MGGSATGIFD- KR14 - 14R 18L 25C 27A 38V 60R 73F 106L 115R 117D |
| BL22P1B11 - MGGSATGIFD | Acrylodan | Rhodamine Red X-SE | | | MGGSATGIFD- KR14 - 14R 18L 25C 27A 38V 60R 73F 106L 115R 117D |
| BL22P1B11 - MGGSATGIFD | Acrylodan | SPDP + Rhodamine Red X-SE | | | MGGSATGIFD- KR14 - 14R 18L 25C 27A 38V 60R 73F 106L 115R 117D |
| BL22P2D4 | Acrylodan | | | | MGI-KR14-14R 18L 25C 27A 38V 60R 73F 106V 115R 117D |
| BL22P2F3 | Acrylodan | | | | MGI-KR14-14R 18L 25C 27A 38V 60R 73F 106A 115R 117D |
| Second unattached (free) fluorophore | | | | | |
| BL10P26E7 | Acrylodan | Rhodamine B | 19 | 0 | MGI - KR14 - 14F 18L 27C 60R 73F 106V 116R 117D |
| BL22P1 B11 | Acrylodan | Rhodamine B | 16 | 0 | MGI - KR14 - 14R 18L 25C 27A 38V 60R 73F 106L 115R 117D |

Example 11

Immobilized Bilirubin Probes

TABLE 8

All proteins are based on SEQ 3 and therefore have an additional 6 His tag at the C terminus. N-terminal modification sequences replace the N-terminal methionine of the template sequence (i.e. sequence X changes MGIFD (SEQ ID NO: 38) to X-GIFD (SEQ ID NO: 64)).
C-terminal modification sequences replace the C-terminal six histidine tag of the template sequence (i.e. sequence Y changes RRDRGHHHHHH (SEQ ID NO: 65) to RRDRG-Y (SEQ ID NO: 66)).

Fluorophores derivatized to 25K included acrylodan, Biotum, Kodak X-Sight, and the LiCor IR dyes of Table 3.

| Construct | N-terminal Modification Sequence | C-terminal Modification Sequence |
|---|---|---|
| CHEMICAL LINKAGE THROUGH LYSINE | | |
| BL22P1B11_25C-7K | | |
| BL22P1B11_25C_7K, 37K, 46K, 50K | | |
| BL22P1B11_25C_7K, 37K, 46K, 50K, 88K, 92K | | |
| BL22P1B11_25C_7K, 37K, 46K, 50K, 129K, 130K | | |
| BL22P1B11_25C_7K, 37K, 46K, 50K, 88K, 92K, 129K, 130K | | |
| CHEMICAL LINKAGE THROUGH CYSTEINE | | |
| BL22P1B11_25K_3C | | |
| BL22P1B11_25K_7C | | |
| BL22P1B11_25K_46C | | |
| BL22P1B11_25K_50C | | |
| BL22P1B11_25K_67C | | |
| BL22P1B11_25K_83C | | |
| BL22P1B11_25K_109C | | |
| The following clones are N-terminal mutants of BL22P1B11_25K | | |
| BL23P1A8_25K | MGACSGG | (SEQ ID NO: 4) |
| BL23P1B10_25K | MGSAGCG | (SEQ ID NO: 5) |

TABLE 8-continued

All proteins are based on SEQ 3 and therefore have an additional 6 His tag at the C terminus. N-terminal modification sequences replace the N-terminal methionine of the template sequence (i.e. sequence X changes MGIFD (SEQ ID NO: 38) to X-GIFD (SEQ ID NO: 64)).
C-terminal modification sequences replace the C-terminal six histidine tag of the template sequence (i.e. sequence Y changes RRDRGHHHHHH (SEQ ID NO: 65) to RRDRG-Y (SEQ ID NO: 66))

Fluorophores derivatized to 25K included acrylodan, Biotum, Kodak X-Sight, and the LiCor IR dyes of Table 3.

| Construct | N-terminal Modification Sequence | C-terminal Modification Sequence |
|---|---|---|
| BL23P2A7_25K | MGGGGCC | (SEQ ID NO: 6) |
| BL23P2C8_25K | MGGSGGC | (SEQ ID NO: 7) |
| BL23P3A2_25K | MGDTAGC | (SEQ ID NO: 8) |
| BL23P4B2_25K | MGGDCGG | (SEQ ID NO: 9) |
| BL23P4B4_25K | MGGCSGA | (SEQ ID NO: 10) |
| BL23P4B6_25K | MGGGDGC | (SEQ ID NO: 11) |
| BL23P4B7_25K | MGSSNSC | (SEQ ID NO: 12) |
| BL23P4C8_25K | MGSDCAY | (SEQ ID NO: 13) |
| BL23P4E2_25K | MGDTNCG | (SEQ ID NO: 14) |
| BL23P4E7_25K | MGGSGCS | (SEQ ID NO: 15) |
| BL23P4G5_25K | MGGCGCG | (SEQ ID NO: 16) |
| BL23P5A4_25K | MGANACG | (SEQ ID NO: 17) |
| BL23P5B7_25K | MGGGACG | (SEQ ID NO: 18) |
| BL23P5E2_25K | MGGNCGG | (SEQ ID NO: 19) |
| BL23P5H12_25K | MGCGGSC | (SEQ ID NO: 20) |
| BL23P6B5_25K | MGGSTSC | (SEQ ID NO: 21) |
| BL23P6C10_25K | MGDGGCS | (SEQ ID NO: 22) |
| BL23P6C5_25K | MGATSCG | (SEQ ID NO: 23) |
| BL23P6D3_25K | MGASCGY | (SEQ ID NO: 24) |
| BL23P6D9_25K | MGDGACG | (SEQ ID NO: 25) |
| NON-COVALENT LINKAGE | | |
| BL22P1B11_25K_N6C6 | MGHHHHHH (SEQ ID NO: 67) | |
| BL22P1B11_25K_N6C6_G S | MGHHHHHHGGSGSGSG (SEQ ID NO: 68) | GGSGSGSGHHHHHH (SEQ ID NO: 69) |
| BL22P1B11_25K_C2X | | HHHHHHSRAWRHPQFGGHHHHHH (SEQ ID NO: 70) |
| BL22P1B11_25K_C2X_G S | | GGGSGGGSGGGTGGGSGGGRRADAAHHHHHHSRAWRHPQ FGGHHHHHH (SEQ ID NO: 71) |
| BL22P1B11_25K_PS19D5 (PS19-1) | | HHHHHHRAFIASRRIRRP (SEQ ID NO: 72) |
| BL22P1B11_25K_PS19-6L | | HHHHHHRLLLRRLRR (SEQ ID NO: 73) |
| BL22P1B11_25K_PS19-6I | | HHHHHHRIIIRRIRR (SEQ ID NO: 74) |
| The following clones are C-terminal mutants of BL22P1B11_25K | | |
| C2XFFA3H11_25K | | AASHHHHHHSHRATPNTSPHHHHHHH (SEQ ID NO: 75) |
| C2XFFA3B3_25K | | NDNHHHHHHPSNTNHNSNSNHHHHHH (SEQ ID NO: 76) |

Example 12

Measurements of unbound bilirubin and unbound FFA were performed in blood samples, that would otherwise be discarded, obtained from 5 extremely low birth weight (<2000 g) newborns treated with a fat emulsion (Intralipid®) at 3 to 3.5 g/kg/day. Unbound bilirubin measurements were performed using BL22P1B11 (SEQ ID NO: 35)-Rh in plasma samples diluted 25 fold in HEPES buffer. FFAu concentrations were determined in plasma diluted 50 fold in HEPES buffer and measurements were performed as described in [Huber A H, Kampf J P, Kwan T, Zhu B and Kleinfeld A M. Fatty acid-specific fluorescent probes and their use in resolving mixtures of different unbound free fatty acids in equilibrium with albumin. Biochemistry 45: 14263-14274, 2006]. Fluorescence intensities were measured using an FFAu meter as described in [Huber A H, Kampf J P, Kwan T, Zhu B and Kleinfeld A M. Fatty acid-specific fluorescent probes and their use in resolving mixtures of different unbound free fatty acids in equilibrium with albumin. Biochemistry 45: 14263-14274, 2006] for FFAu and the same meter modified for emissions at 525 and 575 nm for Bf. The unbound bilirubin concentrations were determined from the 525/575 nm fluorescence ratios using equation (6). Unbound FFA were performed using ADI-FAB2 as described in Cantor et al [Cantor W J, Hoe Kim H, Jolly S, Moe G, Burstein J M, Mendelsohn A, Kleinfeld A M and Fitchett D. B-Type Natriuretic Peptide and Serum Unbound Free Fatty Acid Levels after Contemporary Percutaneous Coronary Intervention. Journal of Invasive Cardiology 20: 186-188, 2008]. The distribution of FFAu species was estimated for Intralipid® infusion using the approach of [Richieri, G and Kleinfeld, A M, Unbound free fatty acid levels in human serum. Journal of Lipid Research 36:229-240, 1995].

TABLE 9

| Patient | Unbound Bilirubin nM | Unbound FFA nM |
|---|---|---|
| 1 | 33 | 35 |
| 2 | 9 | 20 |
| 3 | 94 | 1270 |
| 4 | 80 | 600 |
| 5 | 30 | 54 |

Although it is known that Intralipid® can increase total FFA and thereby increase unbound bilirubin, the results of Example 12 demonstrate that unbound FFA (FFAu) can increase by much larger factors than total FFA. This results because the ratio of total FFA to albumin increases linearly (about 10 fold in the study of Amin [Amin S B. Effect of free fatty acids on bilirubin-albumin binding affinity and unbound bilirubin in premature infants. *JPEN J Parenter Enteral Nutr* 34: 414-420, 2010] whereas FFAu increase essentially exponentially at large FFA to albumin ratios, more than 1000 fold in Table 9. In Example 12 two of the patients had FFAu levels of 600 and 1200 nM, whereas normal levels are 1-2 nM [Apple F S, Kleinfeld A M and Adams J E. Unbound Free Fatty Acid Concentrations Are Increased in Cardiac Ischemia. *Clinical Proteomics* 1: 41-44, 2004]. At levels even much lower than 600 nM many studies have demonstrated toxic effects of FFA (or FFAu) including cardio toxicity, blocking the immune response as well as deleterious effects on many cellular functions [Kleinfeld A M and Okada C. Free fatty acid release from human breast cancer tissue inhibits cytotoxic T-lymphocyte-mediated killing. *J Lipid Res* 46: 1983-1990, 2005; Oliver M F. Sudden cardiac death: the lost fatty acid hypothesis. *QJM* 99: 701-709, 2006]. Only by monitoring FFAu levels during Intralipid® infusion can those infants at risk for FFAu toxicity be identified.

The major (>75%) FFA species generated from Intralipid® are linoleic, oleic, palmitic and linolenic FFA. Because ADIFAB2 is most specific for stearic acid, for which Intralipid® contains only between 1.5 and 5.5%, FFAu probes with specificity for linoleic, oleic, palmitic and linolenic FFA will provide more accurate and sensitive detection of the rise in plasma FFAu due to Intralipid® hydrolysis. Such FFAu probes have been produced (Table 10) using the methods described in U.S. Pat. No. 7,601,510 and U.S. publication 2010/0298162 and in [Huber A H, Kampf J P, Kwan T, Zhu B and Kleinfeld A M. Fatty acid-specific fluorescent probes and their use in resolving mixtures of different unbound free fatty acids in equilibrium with albumin. *Biochemistry* 45: 14263-14274, 2006]. Sensitive FFAu probes are necessary for detecting the rise in the patient's FFAu levels, early in the titration of Intralipid®, which is critical for the prevention of unbound bilirubin and FFAu from reaching toxic levels.

TABLE 10

FFAu probes for measuring FFAu levels in Intralipid ® treated patients

| | | KD (nM) | | | |
|---|---|---|---|---|---|
| Clone | Mutations | LA | OA | PA | SA |
| ADIFAB2 | 72A | 105.1 | 21.5 | 19.5 | 7.6 |
| L19CP10C7 | MGI- 14R 18L 27C 71I 73F 117D | 0.8 | 1.2 | 7.5 | 1.9 |
| L138P1H8 N24C | MGI- 18L 21L 23Y 24C 31I 55V 72S 73S 74G 76V 117H 128Y | 6.5 | 7.6 | 34.2 | 12.6 |
| L22P5E11 | 38R 69T 72A 73K 106A | 6.7 | 3.1 | 18.3 | 2.2 |
| L61P8 B12 | 8I 14L 18L 23L 27Y 30C 31V 53I 55W 72G 73T 74A 78V 82V 91Y 93M 102V 106W 115W 117L | 25.7 | 4.3 | 8.5 | 15.0 |
| L4BP4B9 | 73W 74S | 40.8 | 18.9 | 2.9 | 12.6 |
| L119P3E5 | 18V 27C 31A 72A 73W | 23.0 | 12.7 | 4.0 | 7.4 |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A composition comprising (a) a probe that binds to bilirubin but does not bind significantly to fatty acid comprising an intracellular lipid binding protein (iLBP) mutein labeled with a first fluorophore, wherein the iLBP mutein corresponds to SEQ ID NO: 3 comprising one or more amino acid substitutions at positions selected from the group consisting of positions 14, 18, 23, 25, 27, 31, 36, 38, 55, 60, 72, 73, 74, 78, 102, 104, 106, 115 and 117, and wherein the first fluorophore is attached to a lysine residue, the N-terminus amino group of the iLBP, or to a cysteine substitution, and (b) a second fluorophore, wherein the second fluorophore is free in solution or attached to a protein which does not bind bilirubin, and wherein the first fluorophore and the second fluorophore are capable of excitation at the same wavelength, and wherein the emission wavelength of the first fluorophore and the second fluorophore are different, and wherein the second fluorophore does not change its emission in response to bilirubin binding to the iLBP mutein.

2. The composition of claim 1, wherein the iLBP mutein is SEQ ID NO: 35.

3. The composition of claim 1, wherein the iLBP mutein further comprises substitutions 7R 20R 46R 100R 125R and 130R.

4. The composition of claim 1, wherein the iLBP mutein further comprises substitutions 7R 16R 20R 29R 37R 46R 50R 88R 92R 94R 100R 125R 129R and 130R.

5. The composition of claim 1, wherein the N terminus of the iLBP AFD is substituted with SEQ ID NO: 38, SEQ ID NO: 39, SEQ ID NO: 40, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, or SEQ ID NO:25.

6. The composition of claim 1, wherein the first fluorophore is acrylodan and the second fluorophore is selected from the group consisting of Rhodamine B, NBD, Lucifer yellow, Texas Red, a Bodipy dye and an Alexa Fluor dye.

7. The composition of claim 1, wherein the first fluorophore is LiCor 700DX and the second fluorophore is, Texas Red or an Alexa fluor dye, or a Bodipy dye.

8. The composition of claim 1, wherein the emission intensity of the fluorophores is not affected by the absorbance of blood components selected from bilirubin and hemoglobin.

9. The composition of claim 1, wherein the first fluorophore is attached to a cysteine and is selected from the group consisting of acrylodan, danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA) and the second fluorophore is selected from the group consisting of Alexa Fluor dyes, Bodipy, fluorescein derivatives, rhodamine derivatives and Texas Red.

10. The composition of claim 1, wherein the first fluorophore is attached to a lysine and is selected from the group consisting of acrylodan, Biotium CF750SE, Kodak X-Sight 670 LSS dye, Licor IR Dye 680 LT and Licor IR Dye 700DX and the second fluorophore is selected from the group consisting of Alexa Fluor dyes, Bodipy, fluorescein derivatives, rhodamine derivatives and Texas Red.

11. The composition of claim 1, wherein the protein which does not bind bilirubin is an acceptor protein or peptide domain which is selected from the group consisting of SNAP-tag, CLIP-tag, and ACP-tag.

12. A solid substrate comprising the composition of claim 1 attached to the solid substrate, wherein the solid substrate is a polystyrene or latex bead, Ni-polystyrene, Ni-agarose bead, optionally with iron core, and/or microfluidic device or multiwell plate.

13. The solid substrate of claim 12, wherein the probe is tagged for attachment to the solid substrate, and wherein the tag comprises one or more of His-tag, biotin, Flag-epitope, c-myc epitope, HA-tag, glutathione-S-transferase (GST), maltose binding protein (MBP), a chitin binding domain (CBD), Thioredoxin, β-Galactosidase, VSV-Glycoprotein, calmodulin binding protein, a polystyrene (PS) hydrophobic tag, and a metal affinity tag.

14. The solid substrate of claim 12, wherein the probe comprises a tag and the solid substrate comprises a receptor for the tag.

15. The solid substrate of claim 14, wherein the tag is a poly-histidine tag and the solid substrate comprises an immobilized metal chelate.

16. The composition of claim 1, wherein the iLBP comprises a lysine at position 25 labeled with LI-COR 700DX.

17. The composition of claim 16, attached to a solid support using two His-tags and two linkers.

18. The composition of claim 1, wherein the iLBP comprises one or more tags, wherein the tags are selected from his-tag and PS-tags.

19. A kit comprising:
one or more collection devices for collecting a sample from a patient,
a composition comprising (a) a probe that binds to bilirubin but does not bind significantly to fatty acid comprising an iLBP mutein labeled with a first fluorophore, wherein the iLBP mutein corresponds to SEQ ID NO: 3 comprising one or more amino acid substitutions at positions selected from the group consisting of positions 14, 18, 23, 25, 27, 31, 36, 38, 55, 60, 72, 73, 74, 78, 102, 104, 106, 115 and 117, and wherein the first fluorophore is attached to a lysine residue, the N-terminus amino group of the iLBP, or to a cysteine substitution, and (b) a second fluorophore, wherein the second fluorophore is free in solution or attached to a protein which does not bind bilirubin, and wherein the first fluorophore and the second fluorophore are capable of excitation at the same wavelength, and wherein the emission wavelength of the first fluorophore and the second fluorophore are different, and wherein the second fluorophore does not change its emission in response to bilirubin binding to the iLBP mutein.

20. The composition of claim 1, wherein the iLBP mutein is SEQ ID NO: 36.

21. The composition of claim 2, wherein the second fluorophore is Rhodamine B.

22. The composition of claim 20, wherein the second fluorophores is Rhodamine B.

23. The kit of claim 19, wherein the kit further comprises a reference standard comprising a known concentration of unbound bilirubin.

24. A composition comprising (a) a probe that binds to bilirubin but does not bind significantly to fatty acid comprising an iLBP mutein labeled with a first fluorophore, wherein the iLBP mutein corresponds to SEQ ID NO: 3 comprising one or more amino acid substitutions at positions selected from the group consisting of positions 14, 18, 23, 25, 27, 31, 36, 38, 55, 60, 72, 73, 74, 78, 102, 104, 106, 115 and 117, and wherein the first fluorophore is attached to a cysteine or lysine substitution on the iLBP and wherein the cysteine or lysine substitution is at a position selected from the group consisting of positions 22, 24, 25, 26, 27, 29, 30, 33, 54, 74, 76, 97 and 98, and (b) a second fluorophore, wherein the second fluorophore is free in solution or attached to a protein which does not bind bilirubin, and wherein the first fluorophore and the second fluorophore are capable of excitation at the same wavelength, and wherein the emission wavelength of the first fluorophore and the second fluorophore are different, and wherein the second fluorophore does not change its emission in response to bilirubin binding to the iLBP mutein.

25. The composition of claim 24, wherein the iLBP mutein further comprises substitutions 7R 20R 46R 100R 125R and 130R.

26. The composition of claim 24, wherein the iLBP mutein further comprises substitutions 7R 16R 20R 29R 37R 46R 50R 88R 92R 94R 100R 125R 129R and 130R.

27. The composition of claim 24, wherein the N terminus of the iLBP AFD is substituted with SEQ ID NO: 38, SEQ ID NO: 39, SEQ ID NO: 40, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, or SEQ ID NO: 25.

28. The composition of claim 24, wherein the C-terminus His-tag of SEQ ID NO: 3 is replaced with one or more linkers in combination with one or two 6-His tag wherein the linkers are selected from SEQ ID NO: 26, SEQ ID NO: 27, SEQ ID NO: 28, SEQ ID NO: 29, SEQ ID NO: 30, SEQ ID NO: 41, AAS, NDN, SEQ ID NO: 31, SEQ ID NO: 32 and combinations thereof.

29. The composition of claim 1, wherein the C-terminus His-tag of SEQ ID NO: 3 is replaced with one or more linkers in combination with one or two 6-His tag wherein the linkers are selected from SEQ ID NO: 26, SEQ ID NO: 27, SEQ ID NO: 28, SEQ ID NO: 29, SEQ ID NO: 30, SEQ ID NO: 41, AAS, NDN, SEQ ID NO: 31, SEQ ID NO: 32 and combinations thereof.

30. The composition of claim 24, wherein the first fluorophore is acrylodan and the second fluorophore is selected from the group consisting of Rhodamine B, NBD, Lucifer yellow, Texas Red, a Bodipy dye and an Alexa Fluor dye.

31. The composition of claim 24, wherein the first fluorophore is LiCor 700DX and the second fluorophore is, Texas Red or an Alexa fluor dye, or a Bodipy dye.

32. The composition of claim 24, wherein the emission intensity of the fluorophores is not affected by the absorbance of blood components selected from bilirubin and hemoglobin.

33. The composition of claim 24, wherein the first fluorophore is attached to a cysteine and is selected from the group consisting of acrylodan, danzyl aziridine, 4-[N-[(2-iodoacetoxy)ethyl]-N-methylamino]-7-nitrobenz-2-oxa-1, 3-diazole ester (IANBDE), and 4-[N-[(2-iodoacetoxy)ethyl]-N-methylamino-7-nitrobenz-2-oxa-1,3-diazole (IANBDA) and the second fluorophore is selected from the group consisting of Alexa Fluor dyes, Bodipy, fluorescein derivatives, rhodamine derivatives and Texas Red.

34. The composition of claim 24, wherein the first fluorophore is attached to a lysine and is selected from the group consisting of acrylodan, Biotium CF750SE, Kodak X-Sight 670 LSS dye, Licor IR Dye 680 LT and Licor IR Dye 700DX and the second fluorophore is selected from the group consisting of Alexa Fluor dyes, Bodipy, fluorescein derivatives, rhodamine derivatives and Texas Red.

35. The composition of claim 24, wherein the protein which does not bind bilirubin is an acceptor protein or peptide domain which is selected from the group consisting of SNAP-tag, CLIP-tag, and ACP-tag.

36. A solid substrate comprising the composition of claim 24 attached to the solid substrate, wherein the solid substrate is a polystyrene or latex bead, Ni-polystyrene, Ni-agarose bead, optionally with iron core, and/or microfluidic device or multiwell plate.

37. The solid substrate of claim 36, wherein the probe is tagged for attachment to the solid substrate, and wherein the tag comprises one or more of His-tag, biotin, Flag-epitope, c-myc epitope, HA-tag, glutathione-S-transferase (GST), maltose binding protein (MBP), a chitin binding domain (CBD), Thioredoxin, β-Galactosidase, VSV-Glycoprotein, calmodulin binding protein, a polystyrene (PS) hydrophobic tag, and a metal affinity tag.

38. The solid substrate of claim 36, wherein the probe comprises a tag and the solid substrate comprises a receptor for the tag.

39. The solid substrate of claim 38, wherein the tag is a poly-histidine tag and the solid substrate comprises an immobilized metal chelate.

40. The composition of claim 24, wherein the iLBP comprises a lysine at position 25 labeled with LI-COR 700DX.

41. The composition of claim 40, attached to a solid support using two His-tags and two linkers.

42. The composition of claim 24, wherein the iLBP comprises one or more tags, wherein the tags are selected from his-tag and PS-tags.

43. The kit of claim 19, wherein the iLBP mutein comprises SEQ ID NO: 35 or SEQ ID NO: 36.

44. A kit comprising:
one or more collection devices for collecting a sample from a patient,
a composition comprising (a) a probe that binds to bilirubin but does not bind significantly to fatty acid comprising an iLBP mutein labeled with a first fluorophore, wherein the iLBP mutein corresponds to SEQ ID NO: 3 comprising one or more amino acid substitutions at positions selected from the group consisting of positions 14, 18, 23, 25, 27, 31, 36, 38, 55, 60, 72, 73, 74, 78, 102, 104, 106, 115 and 117, and wherein the first fluorophore is attached to a lysine residue, the N-terminus amino group of the iLBP, or to a cysteine substitution, and (b) a second fluorophore, wherein the second fluorophore is free in solution or attached to a protein which does not bind bilirubin, and wherein the first fluorophore is attached to a cysteine or lysine substitution on the iLBP and wherein the cysteine or lysine substitution is at a position selected from the group consisting of positions 22, 24, 25, 26, 27, 29, 30, 33, 54, 74, 76, 97 and 98 and wherein the second fluorophore are capable of excitation at the same wavelength, and wherein the emission wavelength of the first fluorophore and the second fluorophore are different, and wherein the second fluorophore does not change its emission in response to bilirubin binding to the iLBP mutein.

45. The kit of claim 44, wherein the kit further comprises a reference standard comprising a known concentration of unbound bilirubin.

\* \* \* \* \*